US009687483B2

(12) United States Patent
McKerracher et al.

(10) Patent No.: US 9,687,483 B2
(45) Date of Patent: Jun. 27, 2017

(54) TREATMENT OF CEREBRAL CAVERNOUS MALFORMATIONS AND CEREBRAL ANEURYSMS WITH RHO KINASE INHIBITORS

(71) Applicant: BioAxone BioSciences, Inc., Cambridge, MA (US)

(72) Inventors: Lisa McKerracher, Dania Beach, FL (US); Lisa M. Bond, Braintree, MA (US)

(73) Assignee: BIOAXONE BIOSCIENCES, INC., Cambridge, MA (US)

( * ) Notice: Subject to any disclaimer, the term of this patent is extended or adjusted under 35 U.S.C. 154(b) by 0 days.

(21) Appl. No.: 15/006,314

(22) Filed: Jan. 26, 2016

(65) Prior Publication Data

US 2016/0213664 A1    Jul. 28, 2016

Related U.S. Application Data

(60) Provisional application No. 62/107,571, filed on Jan. 26, 2015, provisional application No. 62/185,857, filed on Jun. 29, 2015, provisional application No. 62/286,607, filed on Jan. 25, 2016.

(51) Int. Cl.
| | | |
|---|---|---|
| *A61K 31/47* | (2006.01) | |
| *A61K 31/4725* | (2006.01) | |
| *A61K 31/551* | (2006.01) | |
| *A61K 31/4545* | (2006.01) | |

(52) U.S. Cl.
CPC ...... *A61K 31/4725* (2013.01); *A61K 31/4545* (2013.01); *A61K 31/551* (2013.01)

(58) Field of Classification Search
CPC ..... A61K 31/47; C07D 217/22; C07D 215/38
USPC ........................................................ 514/310
See application file for complete search history.

(56) References Cited

U.S. PATENT DOCUMENTS

| | | | |
|---|---|---|---|
| 4,997,834 A | 3/1991 | Muro et al. | |
| 6,140,333 A | 10/2000 | Tsuchiya et al. | |
| 7,572,913 B2 * | 8/2009 | McKerracher | ....... C07D 211/58 546/141 |
| 8,957,003 B2 | 2/2015 | Wu et al. | |
| 2003/0120511 A1 | 6/2003 | Legnini | |
| 2011/0112035 A1 * | 5/2011 | Jorgensen | ............ C07K 14/475 514/17.8 |

FOREIGN PATENT DOCUMENTS

| | | |
|---|---|---|
| CA | 2304981 | 5/1999 |
| CA | 2325842 | 8/2007 |

OTHER PUBLICATIONS

Borikova et al. (2010) Rho Kinase Inhibition Rescues the Endothelial Cell Cerebral Cavernous Malformation Phenotype, J. Biol. Chem. 285(16)11760-11764.

(Continued)

*Primary Examiner* — San-Ming Hui
(74) *Attorney, Agent, or Firm* — Ann-Louise Kerner; Morse, Barnes-Brown & Pendleton, P.C.

(57) ABSTRACT

Provided are methods of treating a cerebral cavernous malformation (CCM) and methods of treating cerebral aneurysm in a mammal with certain Rho kinase inhibitors.

10 Claims, 9 Drawing Sheets

(56) References Cited

OTHER PUBLICATIONS

Eldawoody et al. (2009) Simplified experimental cerebral aneurysm model in rats: comprehensive evaluation of induced aneurysms and arterial changes in the circle of Willis, Brain Res. 1300:159-168.

FDA (2005) Guidance for Industry Estimating the Maximum Safe Starting Dose in Initial Clinical Trials for Therapeutics in Adult Healthy Volunteers (30 pages).

Fukumoto et al. (2005) Acute vasodilator effects of a Rho-kinase inhibitor, fasudil, in patients with severe pulmonary hypertension, Heart, 91:391-392.

https://clinicaltrials.gov/ct2/show/NCT02317627?term=kd025&rank=2 (4 pages).

Hara et al. (2000) Protein kinase inhibition by fasudil hydrochloride promotes neurological recovery after spinal cord injury in rats, J. Neurosurg. (Spine 1) 93:94-101.

Ishizaki et al. (2000) Pharmacological Properties of Y-27632, a Specific Inhibitor of Rho-Associated Kinases, Mol. Pharmacol. 57:976-983.

Kast et al. (2007) Cardiovascular effects of a novel potent and highly selective azaindole-based inhibitor of Rho-kinase, Brit. J. Pharmacol. 152:1070-1080.

Lee et al. (2014) Selective ROCK2 inhibition in focal cerebral ischemia. Ann. Clin. Transl. Neurol. 1(1):2-14.

Mertsch et al. (2014) Opposing Signaling of ROCK1 and ROCK2 Determines the Switching of Substrate Specificity and the Mode of Migration of Glioblastoma Cells, Mol. Neurobiol., 49:900-915.

Pelosi et al. (2007) ROCK2 and Its Alternatively Spliced Isoform ROCK2m Positively Control the Maturation of the Myogenic Program, Mol. Cell. Biol., 27(17):6163-6176.

Rikitake et al. (2005) Inhibition of Rho Kinase (ROCK) Leads to Increased Cerebral Blood Flow and Stroke Protection Stroke 36(10):2251-2257.

Shi et al. (2013) Rho Kinases in Cardiovascular Physiology and Pathophysiology: The Effect of Fasudil, J. Cardiovasc. Pharmacol. 62:341-354.

Shi et al. (2013) Distinct roles for ROCK1 and ROCK2 in the regulation of cell detachment. Cell Death and Disease 4: e483.

Yi et al. (2015) Photoactivation of hypericin decreases the viability of RINm5F insulinoma cells through reduction in UNK/ERK phosphorylation and elevation of caspase-9/caspase-3 cleavage and Bax-to-Bcl-2 ratio, Biosci Rep. 35:1-13.

Zhao et al. (2011) Efficacy and safety of fasudil in patients with subarachnoid hemorrhage: final results of a randomized trial of fasudil versus nimodipine, Neurol. Med. Chir. (Tokyo) 51:679-683.

http://www.ehealthme.com/drug_side_effects/Fasudil-Hydrochloride-1268381 (3 pages).

http://rsb.info.nih.gov/ij/docs/menus/analyze.html(14 pages).

Hahmann et al. (2010) Rho-kinase inhibitors as therapeutics: from pan inhibition to isoform selectivity, Cell. Mol. Life Sci. 67:171-177.

Jacobs et al. (2006) The Structure of Dimeric ROCKI Reveals the Mechanism for Ligand Selectivity, J. Biolog. Chem. 281(1):260-268.

Newell-Litwa et al. (2015) ROCK1 and 2 differentially regulate actomyosin organization to drive cell and synaptic polarity, J. Cell Biol. 210(2):225-242.

\* cited by examiner

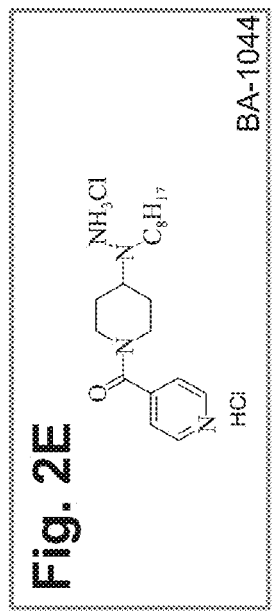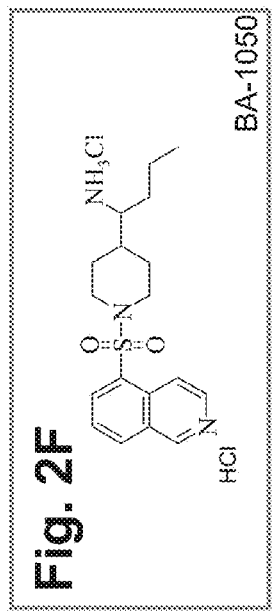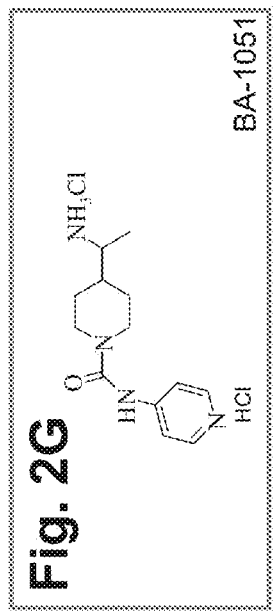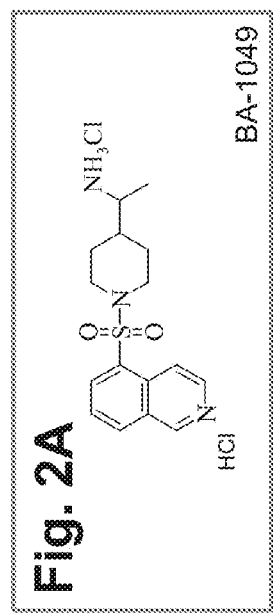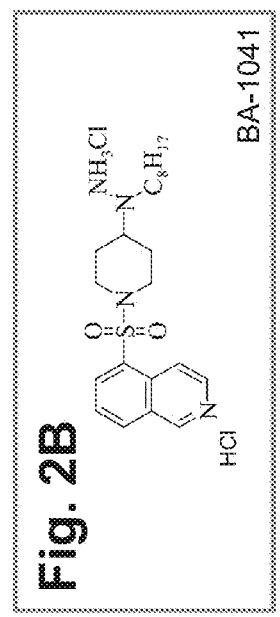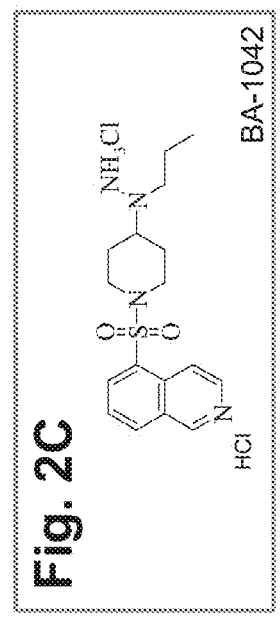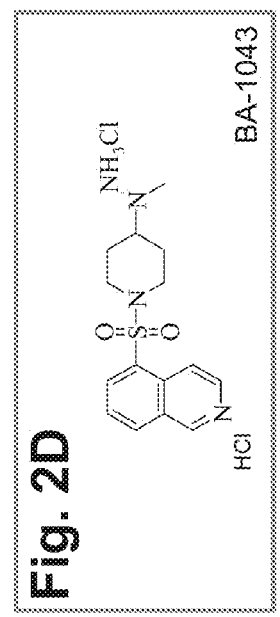

NG-108 cells 400X

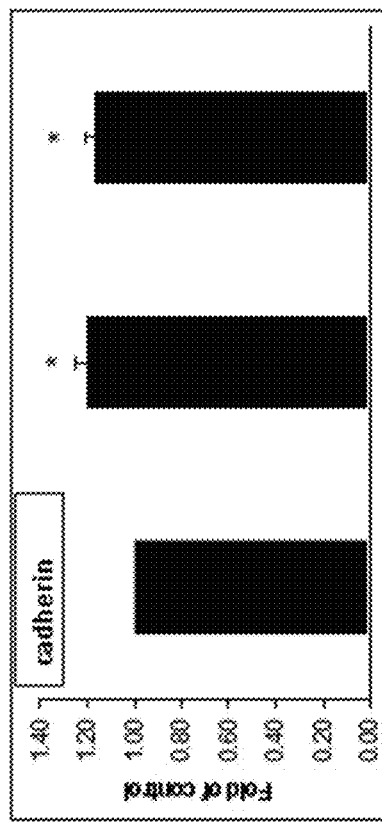
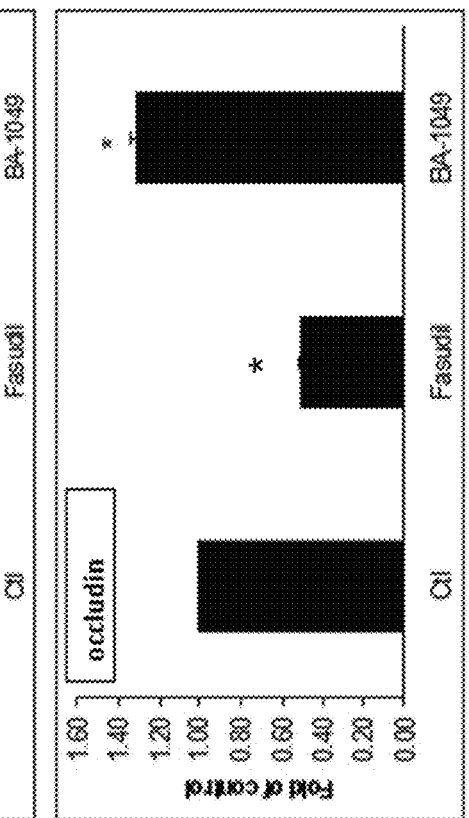
Fig. 7A
Fig. 7B

TREATMENT OF CEREBRAL CAVERNOUS MALFORMATIONS AND CEREBRAL ANEURYSMS WITH RHO KINASE INHIBITORS

CROSS REFERENCE TO RELATED APPLICATIONS

This application claims priority from U.S. Provisional Application No. 62/107,571, entitled "TREATMENT OF CEREBRAL CAVERNOUS MALFORMATIONS AND CEREBRAL ANEURYSMS WITH RHO KINASE INHIBITORS," filed Jan. 26, 2015, U.S. Provisional Application No. 62/185,857, entitled "TREATMENT OF CEREBRAL CAVERNOUS MALFORMATIONS AND CEREBRAL ANEURYSMS WITH RHO KINASE INHIBITORS," filed Jun. 29, 2015, and U.S. Provisional Application No. 62/286,607, entitled "RHO KINASE INHIBITOR BA-1049(R)," filed on Jan. 25, 2016; the entirety of each of which is incorporated by reference herein.

FIELD OF THE INVENTION

The present disclosure relates to the fields of medicine and neurology. More particularly, it relates to the treatment and prophylaxis of cerebral cavernous malformations and cerebral aneurysms, using specific Rho kinase inhibitors.

BACKGROUND OF THE INVENTION

The cerebral vasculature is a complex system of arteries and capillaries whose structure, proper function, and maintenance are inter-regulated. When this regulation malfunctions, either due to genetic predisposition or as the result of external forces, such as hypertension, this system can result in a number of malformations such as cerebral cavernous malformations and cerebral aneurysms.

Cerebral cavernous malformations (CCMs), also called "cavernous angioma" or "cavernoma," are multilobed clusters of grossly dilated and thin-walled capillaries in the brain and spinal cord found in about 0.5% of the population. Patients with CCM lesions usually manifest with headache, epilepsy or hemorrhagic stroke between the ages of 20 and 40 years old. The location and number of lesions in a given individual determines the severity of the overall effect, but the existence of even one lesion may predispose a patient to seizures, stroke, and neurological deficits.

These hyper-permeable vascular lesions consist of a single layer of endothelium with altered sub-endothelial extracellular matrix and no intervening brain parenchyma. CCM lesions range in size from a few millimeters to several centimeters and are susceptible to chronic leakage or large hemorrhagic events. The CCM lesion endothelium bears the typical characteristics of increased vascular permeability. Vascular walls are abnormally thin and dilated and ultrastructural analysis reveals ruptures in the endothelium indicating physical breakage between cells or loss of junctional integrity. Tissue from subjects treated for CCM lesions reveals an absence of tight junctions. The endothelial wall is detached from nearby extracellular matrix, suggesting loss of focal adhesions. Decreased numbers of smooth muscle-like pericytes are observed in association with the capillary walls, and visible pericytes show an abnormal morphology.

CCM lesions can occur due to sporadic or germline loss-of-function mutations in one of three well-characterized genes: CCM1 (KRIT1), CCM2 (malcavernin, MGC4607), or CCM3 (PDCD10). Malformation development requires a two-hit molecular mechanism for pathogenesis; the second hit may be chemical, rather than genetic, such as exposure to cytokines in response to stress or inflammation. Resulting loss of any one of the three CCM proteins can produce the typical lesion phenotype, though CCM3 mutation often results in a more severe phenotype.

At present, there are no approved drugs to prevent the formation, growth, and leakage of cerebral cavernous malformations. The only management option that can be fully curative is surgical resection to remove the lesion. However, the complications of this surgery include permanent or transient neurological morbidity and risk of serious systemic infection. Given the risk-benefit considerations of surgical resection, identified lesions are typically monitored by MRI for signs of lesion expansion and hemorrhage and a resection is conducted only when the surgeon feels that the complications of the untreated lesion (e.g., intractable seizures, progressive neurological deficit) outweigh the surgical risks. Stereotactic radiosurgery may be used if a lesion is both serious and inaccessible by conventional resection, but the benefit to risk ratio is still controversial.

Another malformation is a cerebral aneurysm, which is a localized dilation of a cerebral artery. Cerebral aneurysms are present in 2%-5% of the population, more frequently in women. More than one third of individuals with one aneurysm will develop multiple additional aneurysms. The majority of aneurysms remain dormant and may stay asymptomatic for years, but 0.7% rupture. This rupture can take the form of a temporary leak from the artery or a more serious hemorrhage from a complete opening of the arterial wall. Either form of rupture can be life-threatening and rupture-induced hemorrhage often leads to irreversible neurological sequelae. Indeed, ruptured aneurysms are the leading cause of non-traumatic subarachnoid hemorrhage and cerebral vasospasm.

The most common form of cerebral aneurysm is an intracranial saccular aneurysm, which manifests as a balloon-like outpocketing in the arterial wall up to 30 mm in diameter. An individual aneurysm generally enlarges from an initial smaller (5 mm-10 mm) outpocketing over months or years and larger aneurysms are more likely to rupture. Intracranial aneurysms most commonly occur at the apex of an arterial bifurcation at or near the Circle of Willis, a central network of arteries at the base of the brain. Histopathological examination of aneurysm walls reveals a thinning of the adventitia, media, and intima, with endothelial disruptions and sparse smooth muscle cells.

The standard of care for intracranial aneurysms involves physically isolating the aneurysm from its parent artery by (1) surgical clipping (securing of the aneurysm neck with a metal clip) or, increasingly, (2) endovascular coiling (the insertion of platinum coils into the aneurysm). Complications include intraoperative aneurysm rupture leading to hemorrhage and stroke/hematoma, systemic infection, mechanical vasospasm, and thromboembolism. Pharmaceutical options to prevent formation, growth, or rupture of intracranial aneurysms are lacking. Given the lack of treatment options and the fact that the risks of surgical coiling/clipping may outweigh the natural risk of rupture, preemptive screening for aneurysms is controversial.

Accordingly, what is needed are drugs to prevent and/or treat vascular defects such as CCM and cerebral aneurysms.

SUMMARY OF THE INVENTION

It has been discovered that Rho kinase inhibitor compound(s) can stop CCM formation and/or reduce the number of initial lesions formed in a subject with a mutation in one of the CCM1, CCM2, or CCM3 genes. It has also been discovered that Rho kinase inhibitor compounds can reduce the formation of certain types of cerebral aneurysms.

These discoveries have been exploited to develop the present disclosure, which in part is directed to methods of preventing and treating CCMs, and to methods of treating cerebral aneurysms.

In one aspect, the disclosure provides a method of treating a cerebral cavernous malformation (CCM) in a mammal, comprising: administering to the mammal a therapeutically effective amount of a pharmaceutical formulation comprising BA-1049; and detecting a reduction in the number or size of CCM lesions and/or maturation of simple CCM lesions into complex, clinically significant lesions relative to the number, size, and/or maturity of CCM lesions before administration. In some embodiments, the pharmaceutical formulation is administered orally and is in the form of a tablet or a capsule. In certain embodiments, the formulation comprises the racemic mixture or the (R) enantiomer of BA-0149.

In some embodiments, the method further comprises administering to the mammal a therapeutically effective amount of at least a second Rho kinase inhibitor other than BA-1049. In particular embodiments, the at least a second Rho kinase inhibitor is BA-1041, BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853, or Y27632.

In other embodiments, the formulation administered further comprises an at least a second Rho kinase inhibitor other than BA-1049, such as BA-1041, BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853 or Y27632.

In another aspect, the disclosure also provides a method of treating a cerebral aneurysm in a mammal, comprising: administering to the mammal a therapeutically effective amount of a pharmaceutical formulation comprising BA-1049; and detecting a reduction in the number or the size of cerebral aneurysms and/or a reduction in the maturation of simple aneurysms into complex, clinically significant aneurysms relative to the number, size and/or maturity of the cerebral aneurysms before administration.

In some embodiments, the pharmaceutical formulation comprises the racemic mixture or the (R) enantiomer of BA-1049. In certain embodiments, the formulation is administered orally, and the pharmaceutical formulation is in the form of a tablet or a capsule. In certain embodiments, the method further comprises administering to the mammal a therapeutically effective amount of at least a second Rho kinase inhibitor other than BA-1049. In particular embodiments, the at least a second Rho kinase inhibitor is BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853, and/or Y27632.

In other embodiments, the formulation being administered further comprises a second Rho kinase inhibitor other than BA-1049, such as is BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853 and/or Y27632.

DESCRIPTION OF THE DRAWINGS

The foregoing and other objects of the present disclosure, the various features thereof, as well as the disclosure itself may be more fully understood from the following description, when read together with the accompanying drawings in which:

FIG. 2A is a schematic representation of the structure of rho kinase inhibitor BA-1049;

FIG. 2B is a schematic representation of the structure of rho kinase inhibitor BA-1041;

FIG. 2C is a schematic representation of the structure of rho kinase inhibitor BA-1042;

FIG. 2D is a schematic representation of the structure of rho kinase inhibitor BA-1043;

FIG. 2E is a schematic representation of the structure of rho kinase inhibitor BA-1044;

FIG. 2F is a schematic representation of the structure of rho kinase inhibitor BA-1050;

FIG. 2G is a schematic representation of the structure of rho kinase inhibitor BA-1051;

FIG. 7A is a graphic representation showing the expression of cadherin in HUVEC cells cultured in the presence of nothing (control (ctl)), Fasudil, or BA-1049 (racemic mixture), where * shows treatment is statistically significant from control at $p<0.05$ (T-test);

FIG. 7B is a graphic representation of data obtained from Western blots showing the expression of occludin in HUVEC cells cultured in the presence of nothing (control (ctl)), Fasudil, or BA-1049 (racemic mixture), where * shows treatment is statistically significant from control at $p<0.05$ (T-test);

DESCRIPTION

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

I. Rho Signaling and its Effect on the Cerebral Vasculature

Rho kinases control the activity of Rho, one of five groups of small GTP binding proteins that have GTPase activity. ROCK regulates cell cytoskeleton organization, adhesion, motility, and cycle, and hence Rho kinases regulate these ROCK activities. There are two isoforms of Rho kinase, ROCK I and ROCK II. ROCK I has widespread tissue distribution (but less in brain and skeletal muscle). ROCK II is expressed in brain, heart, and lung, but is relatively low in liver, spleen, kidney, and testes. Both ROCK I and ROCK II are activated by Rho.

Figure 1:
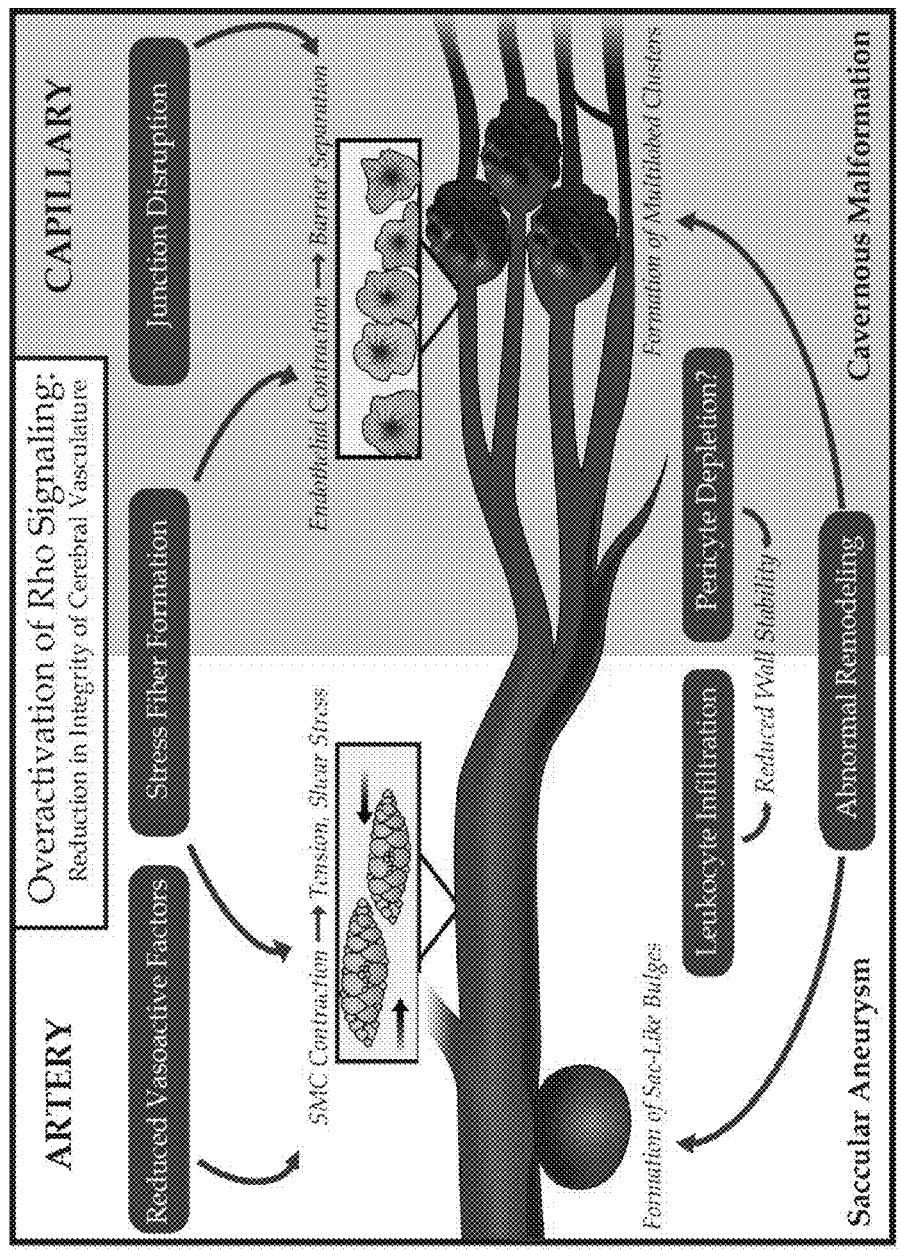
FIG. 1 is a diagrammatic representation of how overactivation of Rho signaling leads to a disruption in the integrity of the cerebral vasculature.

Overactivation of Rho signaling leads to a disruption in the integrity of the cerebral vasculature. This overactivation causes cytoskeletal changes within the endothelial and smooth muscle layers of the cerebral vessel walls that disrupt vascular integrity. In particular, stress fiber formation within endothelial cells upon Rho activation leads to cell contraction and thus gap formation in the endothelial barrier; this is exacerbated by the disruption of intra-endothelial junctions upon Rho overactivation. Stress fiber formation within smooth muscle cells and a reduction in the secretion of vasoactive factors combine to cause vascular contraction and resulting hyper-tension/hemodynamic shear stress. Abnormalities in endothelial remodeling lead to the formation of atypical vascular structures more prone to leakage or rupture. Rho kinase activation also increases invasion by inflammatory leukocytes and resulting wall degradation, and may result in depletion of the smooth muscle-like pericytes that provide structural support to the capillary wall. These Rho kinase-based disruptions in vascular integrity appear to underlie the formation/growth/rupture of aneurysms in cerebral arteries (FIG. 1, left side) and CCMs malformations in cerebral capillaries (FIG. 1, right side).

II. CCMs

On a molecular level, altered remodeling resulting in, e.g., CCM formation, stems directly from the overactivation of Rho signaling in endothelial cells upon knockdown of CCM1/CCM2/CCM3 proteins. Wildtype CCM proteins play a critical role in the down-regulation of Rho signaling: CCM2 has been shown to bind the ubiquitin ligase Smurf1 and localize Smurf1 in a manner that facilitates Rho degradation. Loss of endothelial cell expression of CCM1, CCM2, or CCM 3 results in the activation of RhoA and activation of Rho kinase. This increase in Rho and ROCK activity affects cytoskeletal dynamics and results in the loss of endothelial tube cell formation (Borikova et al. (2010) *JBC* 285:11760-11764). ROCK I and ROCK II affect cytoskeletal dynamics differently. For example, knockdown of expression of ROCK I in glioblastoma cells prevents cell migration, whereas knockdown of ROCK II enhances cell proliferation.

The resulting overactivation of the Rho signaling pathway upon CCM protein knockdown disrupts the dynamic process of blood vessel formation/repair, as Rho signaling directly regulates the cytoskeletal changes underlying endothelial remodeling and migration during angiogenesis and Rho kinase overactivation is associated with pathological angiogenesis. The formation and growth of the dilated and clustered phenotype characteristic of the CCM malformation appears to arise from endothelial instability during vascular remodeling. In particular, CCM1/CCM2/CCM3 protein loss results in impaired angiogenesis, as indicated by defects in vessel-like tube formation and loss of endothelial cell invasion of the extracellular matrix. Angiogenesis occurs in sequential steps that include cell proliferation, cell migration, cell shape rearrangements, and endothelial tube formation. Rho and ROCKI and ROCKII are important for each step and ROCK inhibitors such as Fasudil and BA-1049 differentially affect the separate steps (FIG. 6A-FIG. 9).

Hemorrhage from CCM lesions stems from a disruption in endothelial barrier integrity characterized by (1) increased intracellular actin stress fibers and (2) decreased intra-endothelial junctions. Both of these of hallmarks of vascular leakage are characteristic of dysregulated Rho signaling. Rho overactivation increases intra-endothelial contractility via overactivation of Rho kinase, which leads to the phosphorylation and inactivation of myosin light chain phosphatase and so activation of myosin II and the formation of intracellular stress fibers. When the centripetal tension from the contraction of these stress fibers outbalances the adhesive forces at cell-cell junctions, endothelial cells contract and pull apart from one another, forming gaps in the endothelial barrier. An imbalance in the Rho signaling equilibrium also increases permeability at intra-endothelial junctions; Rho signaling regulates the formation of tight and adherens junctions and Rho kinase overactivation has been shown to promote the adherens junction disruption and tight junction opening necessary for blood leakage through the endothelial barrier.

As demonstrated herein, treatment with Rho inhibitors or ROCK II inhibitors can rescue these endothelial abnormalities and restore vascular stability. Thus CCM lesion growth/repair is intimately linked to a disruption in the Rho equilibrium underlying abnormal vascular remodeling, and inhibition of Rho signaling represents a potent mechanism for preventing or slowing lesion formation/expansion.

III. Cerebral Aneurysms

Systemic arterial hypertension contributes to the development and eventual rupture of saccular aneurysms. Subjects with ruptured intracranial aneurysms are twice as likely to have hypertension as the normal population and the presence of intracranial aneurysm correlates positively with systemic arterial hypertension in general. The role of hypertension in aneurysm pathogenesis is generally viewed as a multifactorial process that involves weakening of the arterial wall due to increased hemodynamic stress.

Rho kinase is substantially involved in the functional and structural alterations of hypertensive blood vessels. Rho kinase inhibitors can reverse hypertension in hypertensive rats. ROCK activation in smooth muscle cells enhances myosin II light chain (MLC) phosphorylation by inhibiting myosin light chain phosphatase. This facilitates actin-activated myosin ATPase activity and so induces actomyosin-mediated contraction within the smooth muscle layer of the arterial wall.

In addition to its role in actomyosin-mediated muscle contraction, Rho kinase is also a key determinant of smooth muscle calcium sensitivity; Rho kinase inhibitors have been shown to induce relaxation of smooth muscle via inhibition of calcium sensitivity. Rho kinase activation also directly inhibits vasodilation: activation of Rho kinase within the endothelial cells of the arterial wall inhibits release of vasoactive factors such as nitric oxide that relax vascular smooth muscle. These observations combine to suggest that Rho kinase inhibition could block the arterial hypertension that contributes to aneurysm development and rupture.

The frictional shear stress on cerebral arterial walls from blood flow through the cerebral vasculature is also implicated in the pathogenesis of intracranial aneurysms. Sustained hemodynamic stresses can result in flow-induced outward vascular remodeling. Intracranial aneurysms are often found in areas with altered hemodynamic stresses (e.g., arterial junctions and bifurcations), and remodeling triggered by abnormal shear stress may underlie aneurysm development. The stress-induced chronic vascular remodeling that contributes to aneurysm formation may also be prevented by Rho kinase inhibition. Hemodynamic shear stress can also induce injury to the endothelial wall of the artery that promotes macrophage invasion, and the wall degradation resulting from this invasion can result in aneurysm pathogenesis.

Inflammation is also a pathogenic process involved in the origin/growth and rupture of saccular aneurysms. The presence of inflammatory cells is found throughout the wall of intracranial aneurysms. This infiltration is positively correlated with risk of aneurysmal rupture. Leukocyte migration from blood vessels into tissue is regulated closely by Rho-mediated events in the endothelial cells of the arterial wall. In particular, leukocyte interactions with endothelial cells stimulate intra-endothelial Rho signaling, inducing stress fiber formation and contractility that leads to gap formation in the endothelial layer. Thus, downregulation of the Rho signaling pathway may also reduce the inflammatory infiltration and resulting arterial wall damage that contributes to aneurysm pathogenesis. Accordingly, Rho and related proteins are targets for prophylactic treatments in families with elevated risk of aneurysm development. In addition, the Rho signaling pathway may also be a target for rupture prevention in identified aneurysms and potentially the long-awaited alternative to surgical coiling or clipping.

IV. Rho Kinase Inhibitor Compounds

The present disclosure provides a method of treating and/or preventing CCM and cerebral aneurysms using a pharmaceutical formulation comprising a Rho kinase inhibitor or antagonist compound, and/or or salts or derivatives thereof, or a combination of more than one Rho kinase inhibitor compound. Such compounds include those known in the art, as well as newly discovered compounds having ROCK activity. Useful Rho kinase inhibitors include, but are not limited to, 4-substratated piperidone derivatives such as those described in U.S. Pat. Nos. 7,572,913 and 6,140,333 (e.g., BA-1049, BA-1041, BA-1042, BA-1043, BA-1044, BA-1050, and BA-1051 (FIG. 2), C3 (U.S. Ser. No. 10/023, 301, CA 2,304,981, and CA 2,325,842), Y27632 [(R)-(+)-trans-4-(1-aminoethyl)-N-(4-pyridyl)cyclohexane-carboxamide as a dihydrochloride salt] which inactivates both ROCK I and ROCK II (Ishizaki et al. (2000) *Mol. Pharmacol.* 57:976; U.S. Pat. No. 4,997,834, KD025 (SLx-2119, *MedChem Express* (HY-15307) Rhopressa, Roclatan, and AR-13533 (Aerie Pharmaceuticals, Inc.), which are combinations of a non-specific ROCK inhibitor with other compounds), Fasudil and HA-1077 (Zhao et al. (2011) *Neurol. Med. Chir.* (Tokyo) 51:679-683) Radicut (edaravone; 3-methyl-1-phenyl-2-pyrazoline-5-one; 5-methyl-2-phenyl-2,4-dihydro-3H-pyrazol-3-one) (Edaravone, Selleckchem), which is known to have kidney toxicity and is only approved in Japan, Biofocus compounds BF66851, BF66852, BF66853 (Biofocus was acquired by Galapagos) and azaindole-based inhibitors of Rho kinase such as 6-chloro-N4-(3,5-difluoro-4-{(3-methyl-1H-pyrrolo{2,3-b}pyridine-4-yl)oxy}-phenyl) pyrimidine-2,4-diamine (azaindolel) (Kast et al. (2007) *Brit. J. Pharmacol.* 152:1070-1080). These compounds are known in the art and can be synthesized by known methods or commercially obtained from available vendors.

BA-1049 and BA-1050 exist as racemic mixtures which can be used for treatment or may be separated into their enantiomers. BA-1049 (R), in particular, is useful for treating CCM and cerebral aneurysms.

A careful balance of Rho activity is required to regulate the actin cytoskeleton for cell shape and motility, and to preserve junctional contacts between cells. Both Rho kinase activation and Rho kinase inhibition can affect the ability of endothelial cells to form tubes, a critical process required for blood vessel formation. The formation of blood vessels is a highly orchestrated process that requires the participation of other cell types, such as pericytes, and signaling by growth factors, such as VEGF. With regard to CCM formation, the imbalance of any of these signals may play a role in the initiation of growth of a CCM. Too much activated Rho and Rho kinase, as in CCM, causes loss of cell-cell junctions and vascular leakiness because it induces stress fiber formation and contraction, causing the cells to pull apart. This lets solutes and blood cells seep between the cells, which is observed in brains of patients with CCM. No Rho activity (i.e., with an overly potent ROCK I/II inhibitor) prevents proliferation and migration of endothelial cells that is required for capillary formation (See Example 10 below).

The balance of inactive Rho to active Rho is important to cell function, and the ratio of ROCK I to ROCK II defines efficacy of ROCK inhibitors and risk/benefit ratios. In fibroblasts, treatment of cells isolated from ROCK I or ROCK II knock-out mice with the pan-ROCK inhibitor Y27632 had differential effects, showing functional differences between ROCK I and ROCK II in regulating the cytoskeleton of fibroblasts (Shi et al. (2013) *Cell Death and Disease* 4:e483). In neurons, inhibition of ROCK II has a more potent effect on promoting neurite outgrowth than ROCK I, and ROCK II is more highly expressed in neurons (U.S. Pat. No. 7,572,913). In endothelial cells, the cell type affected in CCM, there is more ROCK II than ROCK I, and ROCK I and ROCK II inhibitors have differential effects on endothelial cells, as shown below.

V. Therapeutic Pharmaceutical Formulations

The pharmaceutical formulations useful in the therapeutic methods according to the disclosure include a therapeutically effective amount of a Rho kinase inhibitor or antagonist compound.

A "therapeutically effective amount" as used herein refers to that amount which provides a therapeutic and/or prophylactic therapeutic effect for a CCM and/or cerebral aneurysm. If more than one Rho inhibitor compound is part of the pharmaceutical formulation, the therapeutically effective amount may be different for each one, and the addition of one or more of these drugs in the formulation can alter the ratio of the kinase inhibited.

Such formulations can be prepared with a pharmaceutically acceptable carrier in accordance with known techniques, for example, those described in Remington. *The Science And Practice of Pharmacy* (9th Ed., 1995). The term "pharmaceutically acceptable carrier" is to be understood herein as referring to any substance that may, medically, be acceptably administered to a patient, together with a compound of this invention, and which does not undesirably affect the pharmacological activity thereof; a "pharmaceutically acceptable carrier" may thus be for example a pharmaceutically acceptable member(s) selected from the group comprising or consisting of diluents, preservatives, solubilizers, emulsifiers, adjuvant, tonicity modifying agents, buffers as well as any other physiologically acceptable vehicle. This pharmaceutical formulation may further contain additional Rho inhibitors.

The pharmaceutical formulation may be formulated in pharmaceutically acceptable dosage forms such as for injectable use, for oral use, for inhalation use, for transdermal use, for transmembrane use, and the like.

Formulations suitable for oral administration may be presented in discrete units or dosage forms, such as capsules, cachets, lozenges, tablets, pills, powders, granules, chewing gum, suspensions, solutions, and the like. Each dosage form contains a predetermined amount of Rho kinase inhibitor compound. If in the form of a solution, the pharmaceutically acceptable carrier may be an aqueous liquid, such as buffered with a pharmaceutically acceptable pH buffer, or in non-aqueous liquid such as DMSO, or be prepared as an oil-in-water or water-in-oil emulsion.

Injectable dosage forms may be sterilized in a pharmaceutically acceptable fashion, for example, by steam sterilization of an aqueous solution sealed in a vial under an inert gas atmosphere at 120° C. for about 15 minutes to 20 minutes, or by sterile filtration of a solution through a 0.2 μM or smaller pore-size filter, optionally followed by a lyophilization step, or by irradiation of a composition containing a compound of the present invention by means of emissions from a radionuclide source.

A therapeutically effective dosage of the Rho kinase inhibitor compound varies according to inhibitor and varies from patient to patient, and may depend upon factors such as the age of the patient, the patient's genetics, and the diagnosed condition of the patient, and the route of delivery of the dosage form to the patient. A therapeutically effective dose and frequency of administration of a dosage form may be determined in accordance with routine pharmacological procedures known to those skilled in the art. For example, dosage amounts and frequency of administration may vary or change as a function of time and severity of the CCM or cerebral aneurysm. For example, a dosage from about 0.1 mg/kg to 1000 mg/kg, or from about 1 mg/kg to about 100 mg/kg Rho kinase inhibitor may be suitable.

Administration may be by injection into cerebrospinal fluid as a solution or as a suspension suitable for sustained release from the injected pharmaceutical dosage form such as from a vesicle. Administration alternatively may be made to the lesion site by stereotactic injection Reference will now be made to specific examples illustrating the disclosure. It is to be understood that the examples are provided to illustrate exemplary embodiments and that no limitation to the scope of the disclosure is intended thereby.

EXAMPLES

Example 1

Synthesis of an Enantiomer of BA-1049

The following scheme describes the synthesis of 50 mg to 100 mg of an enantiomer of BA-1049 (NT-000077) and includes a chiral synthesis method that enables the identification of the absolute configuration ((R) or (S)) of the molecule.

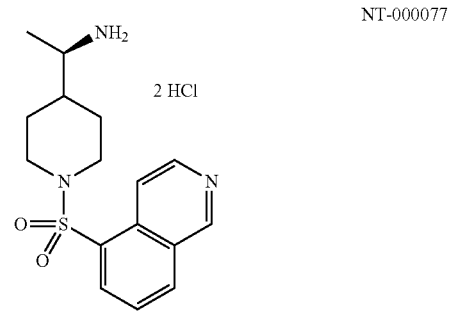 [SMILES: C[C@@H](N)C1CCN(S(=O)(=O)c2cccc3cnccc23)CC1]

NT-000077

To a solution of 1-Benzyloxycarbonyl-4-formylpiperidine (1) (2.0 g, 8.1 mM) in THF (20 mL) was added (S)-2-methylpropane-2-sulfinamide (1.0 g, 8.5 mM) followed by Ti(OiPr)$_4$ (4.45 mL, 16.2 mM). The resulting solution was allowed to stir at room temperature (RT) for 18 hr, and then quenched with saturated aqueous NH$_4$Cl and diluted with EtOAc. The mixture was filtered through a pad of celite, and washed with EtOAc. The layers were separated, and the organic phase was washed with brine, dried (MgSO$_4$) and concentrated to give the crude residue which was purified by column chromatography (Isco 40 g) eluting with a gradient of Hexanes/EtOAc (70/30 to 30/60) to afford the desired imine 2 (2.2 g, 78%).

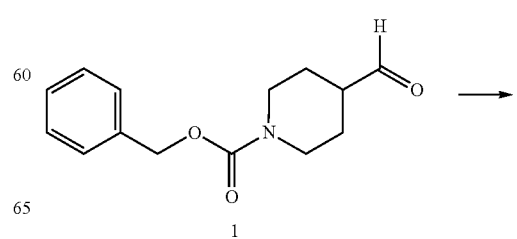

1

-continued

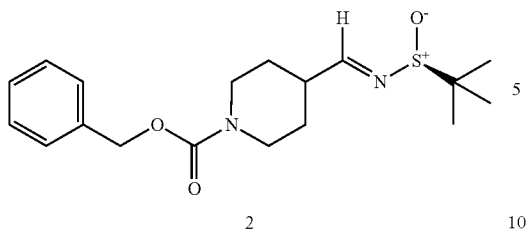

2

To a solution of imine 2 (2.2 g, 6.3 mM) in CH$_2$Cl$_2$ (20 mL) at −78° C. was added MeMgBr (3.1 mL, 3.0 M in Et$_2$O, 9.3 mM). The reaction was maintained at −78° C. for 1 hr, and then allowed to warm slowly to RT overnight. The reaction was quenched with saturated aqueous NH$_4$Cl and diluted with EtOAc and the layers were separated. The organic layer was washed with saturated aqueous NaHCO$_3$, brine, dried (MgSO$_4$) and concentrated. The crude residue was purified by column chromatography (Isco 80 g) eluting with a gradient of Hexanes/EtOAc (70/30 to 10/90) to afford the desired material 3 (1.67 g, 73%).

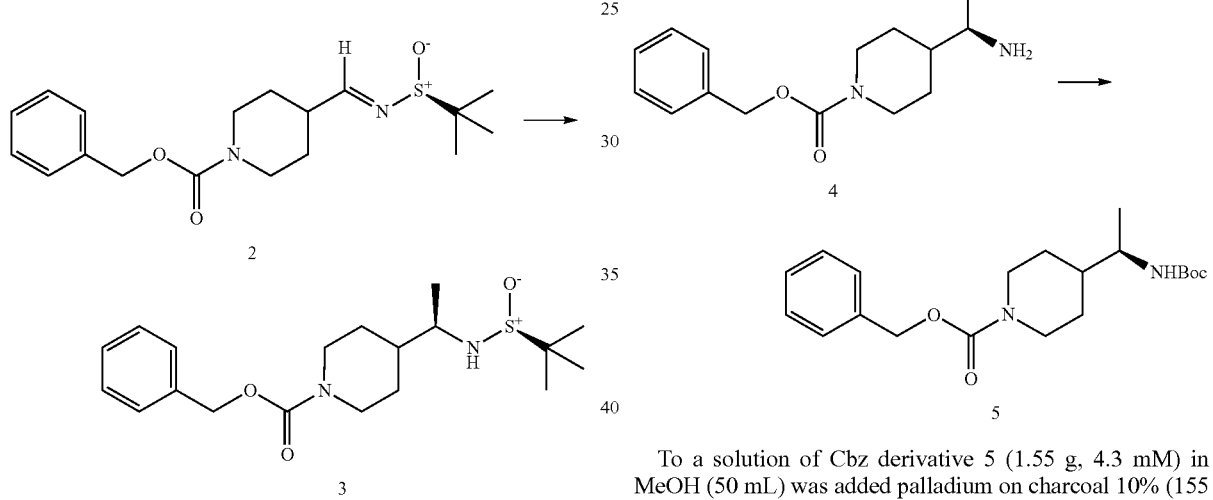

To a solution of sulfinamide 3 (1.67 g, 4.56 mM) in MeOH (50 mL) was added HCl (25 ml, 4M in dioxane, 6.25 mM). The reaction was aged at RT monitoring disappearance of starting material by analytical reverse-phase HPLC. When the starting material was consumed, the reaction was concentrated in vacuo. The crude residue was diluted with EtOAc and the organic layer was washed with saturated aqueous NaHCO$_3$, brine, dried (MgSO$_4$) and concentrated. The crude residue 4 was used as such in the next step. (1.16 g, 97%).

-continued

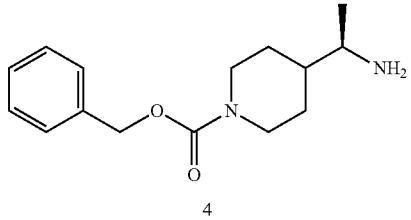

4

To a solution of amine 4 (1.16 g, 4.4 mM) in CH$_2$Cl$_2$ (50 mL) was added DIPEA (0.77 ml, 4.4 mM) followed by Boc$_2$O (3.2 g, 14.6 mM). The resulting solution was allowed to stir at RT overnight. The reaction was then quenched with water and diluted with EtOAc. The layers were separated and the organic phase was washed with saturated aqueous NaHCO$_3$, brine, dried (MgSO$_4$) and concentrated to give the crude derivative which was purified by column chromatography (Isco 80 g) eluting with a gradient of Hexanes/EtOAc (90/10 to 50/50) to afford the desired material 5 (1.55 g, 97%).

To a solution of Cbz derivative 5 (1.55 g, 4.3 mM) in MeOH (50 mL) was added palladium on charcoal 10% (155 mg). The resulting suspension was purged twice with hydrogen and the reaction was allowed to stir at RT overnight under 1 atmosphere of hydrogen. The reaction was purged with nitrogen then diluted with CH$_2$Cl$_2$, filtered through celite and concentrated to give the crude derivative 6 which was used as such in the next step (0.98 g, quant.).

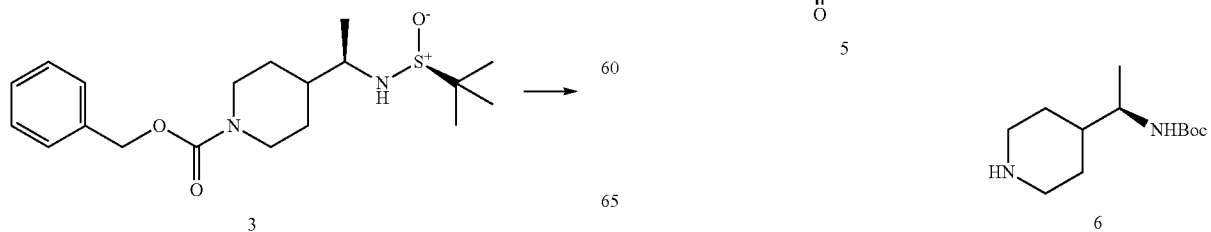

To a flask containing 5-isoquinolinesulfonic acid (5 g, 24 mM) was added $SOCl_2$ (22 ml, 300 mM) followed by a catalytic amount of DMF (0.25 ml). The resulting mixture was allowed to stir at reflux for 4 hr. It was then cooled down and concentrated in vacuo. The residue was purified by trituration with $CH_2Cl_2$ to yield the desired sulfonyl chloride 8 as a white solid (4.2 g, 66%).

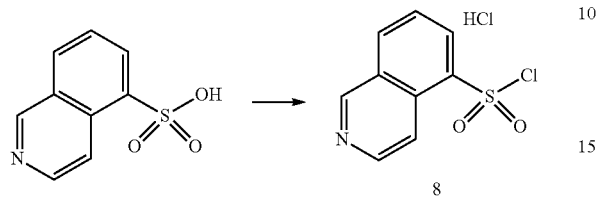

To a solution of amine 6 (1.0 g, 4.4 mM) in $CH_2Cl_2$ (50 mL) was added DIPEA (2.3 ml, 13.1 mM) followed by the sulfonyl chloride 8 (1.73 g, 6.6 mM). The resulting solution was allowed to stir at RT overnight. The reaction was then quenched with water and diluted with EtOAc. The layers were separated and the organic phase was washed with saturated aqueous $NaHCO_3$, brine, dried ($MgSO_4$) and concentrated to give the crude derivative which was purified by column chromatography (Isco 80 g) eluting with a gradient of Hexanes/EtOAc (70/30 to 100%) to afford the desired material 7. An analytical sample injected on a chiral HPLC showed an enantiomeric excess of 95%. Recrystallization from $CH_2Cl_2/Et_2O$/Hexanes affords the desired material 7 as a white solid and with ee >99%. (750 mg, 41%).

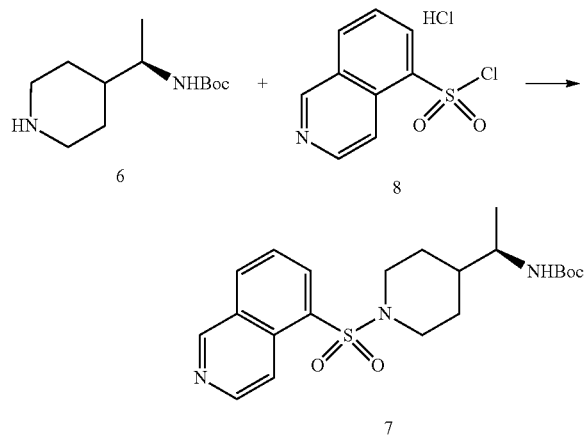

To a solution of the Boc derivative 7 (0.75 g, 1.8 mM) in $CH_2Cl_2$ (15 mL) was added HCl (4 M in dioxane, 5 ml, 20 mM). The reaction was stirred at RT overnight. The reaction was then concentrated in vacuo. The crude residue was diluted with a minimum of MeOH and added slowly to a flask containing $Et_2O$. The heterogeneous mixture was stirred for 5 min then filtered to provide NT-000077 as a white solid (650 mg, 93%). $^1H$ NMR ($CH_3OH$-$d_4$, 400 MHz): ☐ 9.97 (1H, s), 9.18 (1H, d, J=6.9 Hz), 8.76-8.81 (3H, m), 8.18 (1H, t, J=7.9 Hz), 3.98-4.01 (2H, br d, J=12 Hz), 3.15 (1H, p, J=6.6 Hz), 2.62 (2H, t, J=12 Hz), 1.79-1.84 (2H, m), 1.57-1.61 (1H, m), 1.40 (2H, qd, J=12, 4.1 Hz), 1.24 (3H, d, J=6.7 Hz).

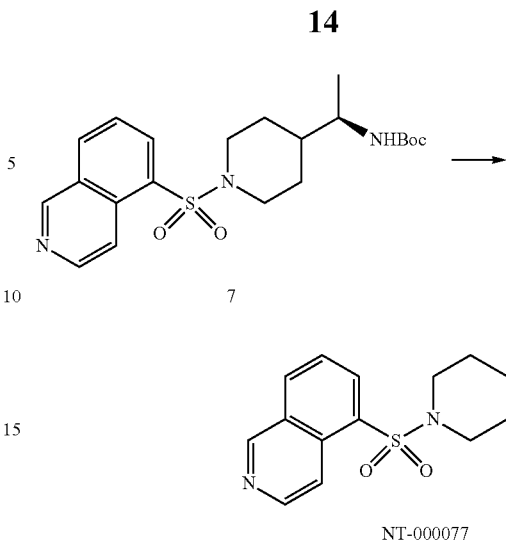

Example 2

In Vitro Effect of Rho Kinase Inhibitors on Vascular Endothelial Cells

The following experiment demonstrates the ability of certain Rho kinase inhibitors to restore key Wildtype (WT) features in vascular endothelial cells depleted of CCM proteins. These in vitro experiments are conducted in endothelial cell lines derived from CCM lesion biopsy in patients with Ccm1, Ccm2, or Ccm3 mutations, and in human microvascular endothelial cell line (HMVEC). The test Rho kinase inhibitors are tested individually and in combination with the commercially available Rho kinase inhibitor Fasudil.

Combinations of different ROCK inhibitors can tune the desired effect on endothelial cells after tube formation and on endothelial cells from patients with cavernous malformations. For example, by combining BA-1049 with Fasudil to give predicted ratio of ROCK I: ROCK II inhibition at ratios of 1:1, 1:10, or 10:1, the effects on the junctional process and stress fibers can be more finely modified. This experiment with endothelial cells from patients with CCM is used to determine the best ratio of ROCK I to ROCK II inhibition to prevent the formation of cavernous malformations.

A. Procedures

1. Cell Line Preparation

Stable cell lines (Wildtype CCM1 Knockdown (KD); CCM2 KD; CCM3 KD) in HMVEC cells (Cell Applications, Inc., San Diego, Calif.) (Cat. #100K-05a) are formed by lentiviral delivery of short hairpin RNA (shRNA) specific to each of the CCM proteins; the Wildtype cell line consists of untreated HMVEC cells. Patient biopsy cell lines (Wildtype, Ccm1 Mutation; Ccm2 Mutation; Ccm3 Mutation) are generated from endothelial cells obtained during biopsies of patients with specific Ccm mutations; the Wildtype cell line is derived from a biopsy sample of a subject with no Ccm mutations.

2. Dosing and Analysis Timing

Five individual doses of each Rho kinase inhibitor (BA-1049 (R), BA-1041, BA-1042, BA-1043, BA-1050) (NuChem Therapeutics, Montreal Canada); Fasudil (Calbiochem, La Jolla, Calif.); Combinations: Fasudil+Each BA Rho kinase inhibitor; Control: Buffer Vehicle) are evaluated for the ability to restore a Wildtype phenotype in each CCM KD HMVEC cell line and each Ccm mutant biopsy cell line. Cell lines are exposed to each dose as: (1) a repeating daily dose in culture media; (2) a 30-min exposure and washout daily; and (3) treatment for an initial 24 hr period only.

Endpoints are evaluated at 24 hr, 48 hr, 72 hr, 96 hr, 120 hr, 144 hr, and 168 hr after initial treatment. Experiments are repeated with Fasudil and with combinations of Fasudil and each individual inhibitor (e.g., Fasudil+BA-1049 (R enantiomer), Fasudil+BA-1042, etc.).

The following endpoints are used to assess the ability of each dose of each Rho kinase inhibitor to restore a Wildtype endothelial phenotype in each cell line at each timepoint.

All experiments are conducted in triplicate and analyzed by two independent assessors blinded to both cell line and treatment.

a. Endothelial Cell Vasculogenesis

Cells are suspended in collagen matrices to permit an analysis of their capacity for vessel-like tube formation. The matrices are made as follows: Collagen is added to tubes containing a mixture of Medium 199 (Life Technologies, ThermoFisher Scientific, Waltham, Mass.) and NaOH at 0° C. Cells are added to a final collagen concentration of 3.75 mg/mL, and the cell-collagen mixture is seeded out into 4.5 mm microwells. The collagen is allowed to gel and equilibrated at 37° C. in a $CO_2$ incubator. After a 3 hr incubation in serum-free culture medium (Medium 199 containing reduced-serum II supplement (Upstate Biotechnology, Lake Placid, N.Y.), bFGF (40 ng/mL), VEGF (40 ng/mL), phorbol ester (50 ng/mL), and ascorbic acid (50 µg/mL), cultures are fixed with 3% gluteraldehyde for 30 min.

Time-lapse fluorescence microscopy is conducted to collect images of cultures at 0 hr, 3 hr, 6 hr, 9 hr, 12 hr, 16 hr, 20 hr, and 24 hr after fixation. Vacuole and lumen area over time is traced and quantified using MetaMorph imaging software (Molecular Devices Corp., Sunnyvale, Calif.) (n=5 independent fields per timepoint), and the number of lumens per field at 24 hr is counted (n=5 independent fields).

b. Endothelial Cell Migration

Haptotactic migration is examined as follows: 20,000 cells are seeded into the upper well of a Boyden chamber (Neuro Probe, Gaithersburg, Md.) in endothelial growth medium-2 (Lonza, Walkersville, Md.) and allowed to migrate for 3 hr into a polycarbonate membrane (8 µM pores) (Sigma-Aldrich, St. Louis, Mo.) coated on the lower surface with human fibronectin (1 µg/mL) (Biomedical Technologies, Ward Hill, Mass.).

After removal of nonmigrated cells, membranes are fixed and stained (Hema3 kit, Fisher Scientific, Waltham, Mass.), and mounted on glass slides. The number of migrated cells per high-power microscopy field is quantified (n=10 fields per condition).

c. Endothelial Cell Permeability

The permeability of endothelial cells to horseradish peroxidase is measured using a trans-well assay as follows:

Trans-well inserts (48-well, 3 µM pore) (Corning Inc., Corning, N.Y.) are coated with human fibronectin and seeded with 30,000 cells per well. Horseradish peroxidase (25 µg/mL) is added to the top of the insert and allowed to permeate for 6 hr. After 6 hr, the solution from the bottom of each well is mixed with 0.1 mL guaiacol and 0.2 mL hydrogen peroxide and measured for absorbance at A490 nm (n=6 wells each).

d. Intra-Endothelial Rho Kinase Activity

Intra-endothelial ROCK activity is assessed by measuring levels of phosphorylated myosin light chain 2 (phospho-MLC2) as follows:

Sub-confluent cells are collected and lysed in RIPA Lysis Buffer (Santa Cruz Biotechnology, Inc., Dallas, Tex.). Cell lysates are analyzed by SDS-PAGE (7% gel) and Western blot using an antibody specific to phosphorylated myosin light chain 2 (Cell Signaling Technology, Danvers, Mass.) (3674). Horseradish peroxidase (HRP)-conjugated secondary antibodies are used to permit development and imaging; relative levels of phosphorylated myosin light chain 2 are quantified via a densitometric quantification of band intensity on ImageJ, according to the ImageJ User Manual instructions for Gel Analysis: http://rsb.info.nih.gov/ij/docs/menus/analyze.html#gels.

e. Intra-Endothelial Ratio of ROCK I to ROCK II

The ratio of ROCK I to ROCK II within endothelial cells is assessed as follows: Sub-confluent cells are collected and lysed in RIPA Lysis Buffer (Santa Cruz Biotechnology, Inc.). Cell lysates are analyzed by SDS-PAGE (7% gel) and Western blot using anti-ROCK I and anti-ROCK II antibodies (611136 and 610623) (BD Biosciences, San Jose, Calif.). HRP-conjugated secondary antibodies are used to permit development and imaging; relative levels of ROCK I and ROCK II are quantified via a densitometric quantification of band intensity on ImageJ, according to the ImageJ User Manual instructions for Gel Analysis: http://rsb.info.nih.gov/ij/docs/menus/analyze.html#gel s.

B. Results

Two or more inhibitor combinations (e.g. inhibitor/Fasudil) restore endothelial cell vasculogenesis, migration, permeability, Rho kinase activity, and ROCK I: ROCK II ratio to WT levels when administered according to a tested dosing regimen.

Example 3

Differential Tissue Expression of ROCK I and ROCK II in Neuronal Cell Lines

Two different neuronal cell lines (PC12 and NG108-15) were used to determine subcellular localization of ROCK I and ROCK II. The localization was studied with and without treatment for 24 hr with 10 µM of the Rho kinase inhibitors BA-1049 (racemic mixture (Synthetica Fine Chemicals, Quebec, Canada), Fasudil (Calbiochem), or Y-27632 (Calbiochem).

A. Procedures 40,000 PC12 cells (ATCC, CRL-1721) were seeded on 8-well chamber, poly-L-lysine-coated (10 µg/mL) chamber slide and fixed. 30,000 NGIO8-15 cells (ATCC, HB-12317) were plated on 8-well chamber slide and fixed 16 hr-24 hr later.

After permeabilization, cells were incubated with specific polyclonal antibodies directed against ROCK I or ROCK II. FITC-conjugated rabbit IgG were used to visualize localization with the use of a fluorescent microscope. Results are representative of 2 independent experiments where at least 4 pictures were taken.

Localization of both kinases was observed under a fluorescence microscope using appropriate primary antibodies directed against ROCK I (sc-5560, lot #D1103) (Santa Cruz Biotechnology, Inc.) or ROCK II (sc-5561, lot #C1804) (Santa Cruz Biotechnology, Inc.) and a secondary antibody (FITC-conjugated anti-rabbit IgG (111-095-144, lot#62750) (Jackson ImmunoResearch Labs, West Grove, Pa.). Negative control using only the secondary antibody was also performed for each cell line or tissues analyzed. NG108-15 and PC12 cells seeded in 8-well chamber slides were fixed 30 min with 4% p-formaldehyde, blocked 30 min with 10% normal goat serum and localization determined by immunofluorescence using ROCK I and ROCK II specific primary antibodies (1/50 in 2% goat serum, 1 hr 30 min at RT) and FITC-coupled rabbit IgG (1/200-1/400 in 2% goat serum/PBS, 1 hr at RT). Fluorescence was visualized under a fluorescent microscope using FITC filter. Methanol fixation was tried for but the signal was weak, likely due to loss of ROCK compared to fixation with p-formaldehyde.

B. Results

Figure 3B:
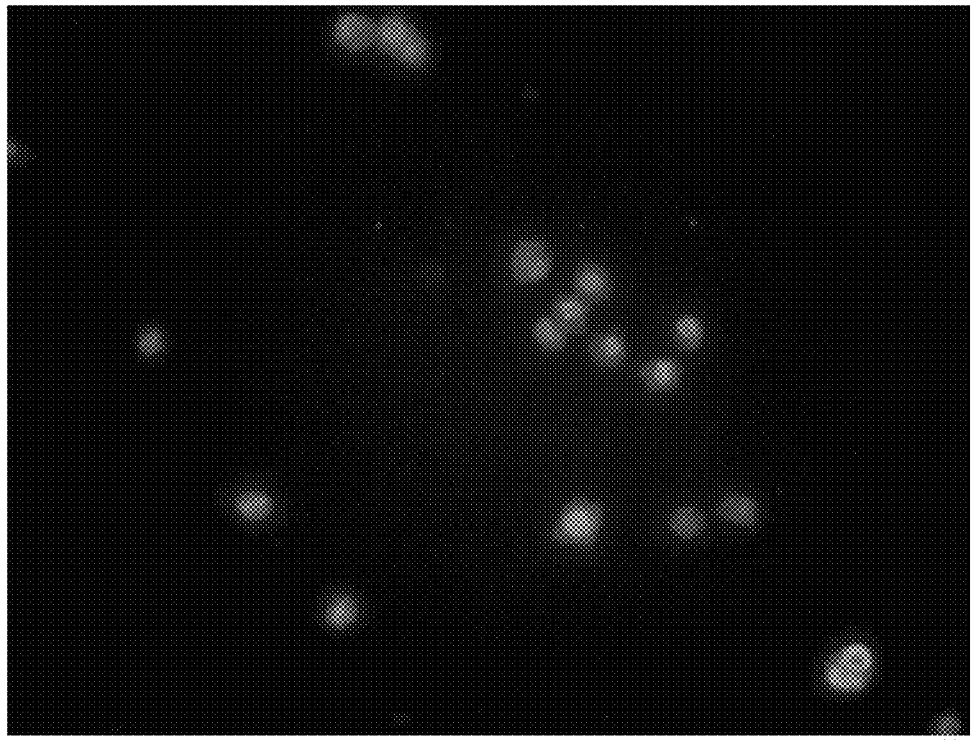
FIG. 3B is a photographic representation of a PC12 cells immunoreacted with antibodies specific to Rock I showing the location of ROCK I in PC12 cells is both cytoplasmic and nuclear.
Figure 3A:
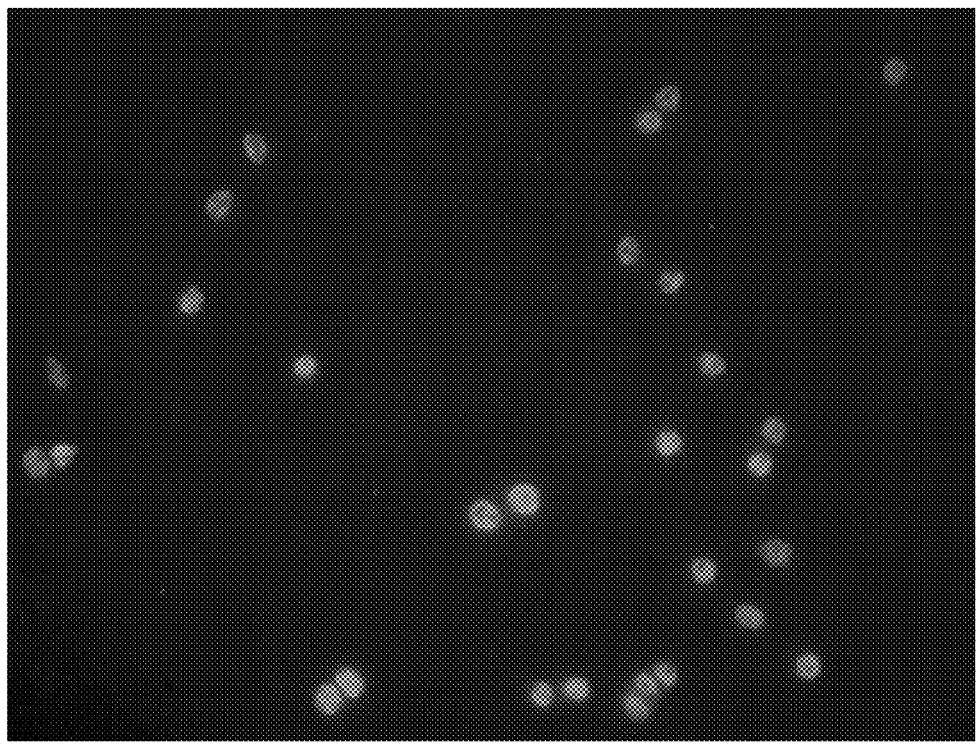
FIG. 3A is a photographic representation of PC12 cells immunoreacted with antibodies specific to ROCKII showing the location of ROCK II in PC12 cells, where the immunofluorescence with anti-ROCKII antibody is predominantly nuclear.

FIG. 3A and FIG. 3B show that in PC12 cells, ROCK II is more associated to the nuclear compartment (FIG. 3A), while ROCK I is expressed throughout the cell (FIG. 3B). A punctate localization associated with the nuclear compartment is also seen.

Figure 4B:
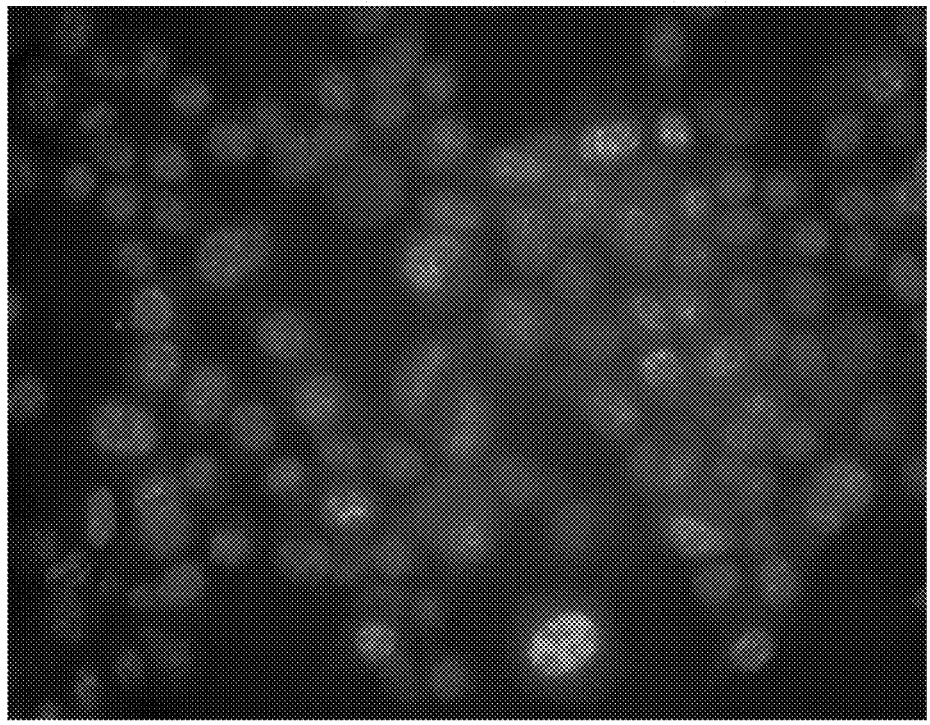
FIG. 4B is a photographic representation (400×) of NG108-15 cells immunoreacted with anti-ROCK II antibody showing diffuse nuclear localization and weak cytoplasmic staining.
Figure 4A:
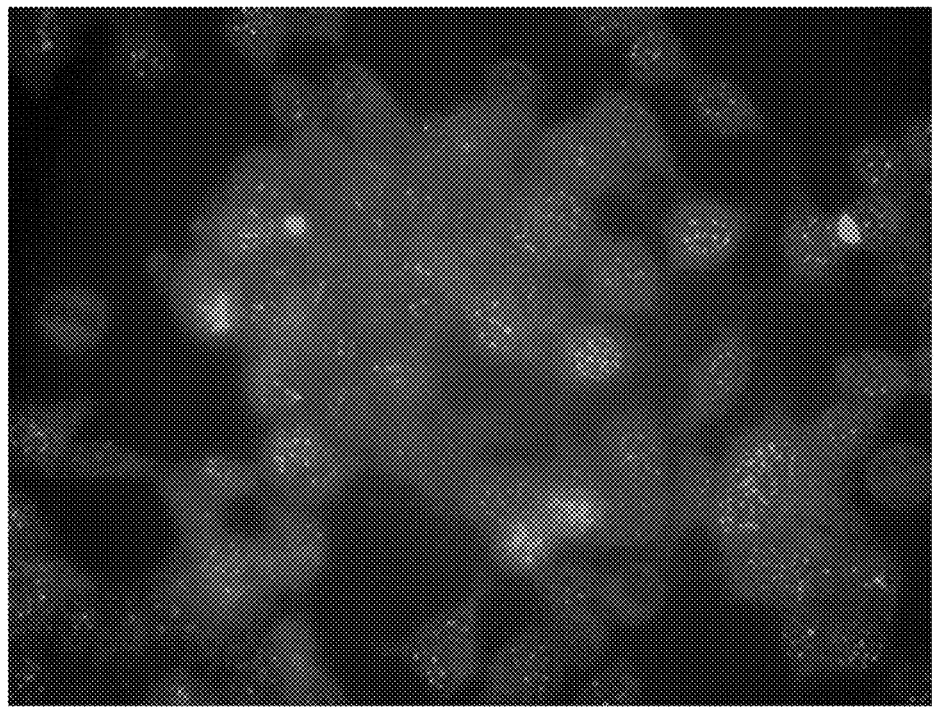
FIG. 4A is a photographic representation (400×) of NG108-15 cells immunostained with anti-ROCK I antibodies showing the location of ROCK I in NG108-15 is punctate in the nucleus and also strongly stains the cytoplasm and neurites.

NG108-15 cells, a neuroblastoma cell line, also show a similar pattern of ROCK I (FIG. 4A) and ROCK II (FIG. 4B) expression where ROCK I has a more punctuate appearance (FIG. 4A) and has more diffuse localization in the cytoplasm.

Example 4

Differential Expression of ROCK I and ROCK II in Tissues and Cell Lines

ROCK1 and ROCK2 expression was evaluated in rat tissues, in NG108 cells (a neuroblastoma cell line), in PC12 cells (an adrenal pheochromocytoma cell line), in HUVEC cells, and in U87 cells (a human glioblastoma cell line).

A. Procedures

Sub-confluent NG108, PC12, HUVEC, and U87 cells were collected and lysed in RIPA-NP-40 buffer (Santa Cruz Biotechnology, Inc.). Rat tissues (kidney, heart, spinal cord, liver, brain, muscle, skin, spleen, retina) were collected and homogenized in lysis buffer. Twenty micrograms of protein was loaded onto 7% SDS-PAGE gels.

Protein expression was visualized by Western blot using primary antibodies directed against ROCK I (sc-5560, lot #D1103, Santa Cruz Biotechnology, Inc., 1/300 in TBS—0.1% Tween 20-3% BSA, 1 hr at RT) or ROCK II (sc-5561, lot #C1804, Santa Cruz Biotechnology, Inc., 1/300 in TBS—0.1% Tween 20-3% BSA, 1 hr at RT) and an HRP-conjugated anti-rabbit secondary antibody (1/20,000 in TBS—0.1% Tween 20-3% skim fat powdered milk, 1 hr at RT). Protein expression was quantified using a densitometer (Molecular Dynamics) set for area analysis.

B. Results

Figures 5, 5A, 5B:
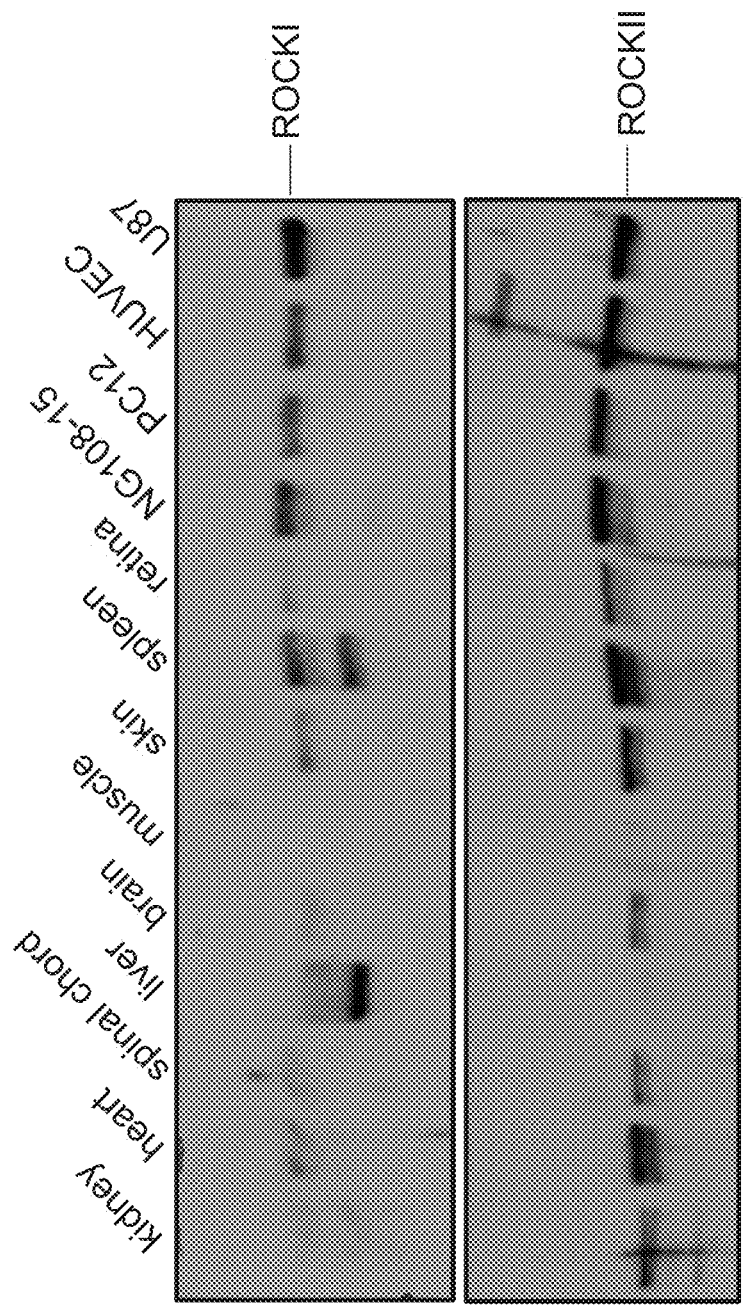
FIG. 5A is a photographic representation of a Western blot showing the expression of ROCK I in different tissues isolated from rat and in various cell lines.
FIG. 5 B is a photographic representation of a Western blot showing the expression of ROCK II in different tissues isolated from rat and in various cell lines.

ROCK I and ROCK II expression in rat tissues (kidney, heart, spinal cord, liver, brain, muscle, skin, spleen, retina), NG108 cells, PC12 cells, HUVEC cells, and U87 cells is presented in FIG. 5. The differential expression of ROCK I vs ROCK II across these tissues and cell lines can be noted; for example, ROCKII is highly expressed in the brain and retina and poorly expressed in the liver, as compared with ROCK I.

Example 5

Selectivity of BA-1049 and Fasudil for ROCK I and ROCK II

The inhibitor potency of BA-1049 (racemic mixture) and Fasudil (Calbiochem) were compared by fluorescent polarization assays performed using a Biomek 2000 robotic workstation (Beckman Instruments, Palo Alto, Calif.) in a 96-well plate format. The assay was performed utilizing the IMAP® ROCK I and ROCK II kits (Molecular Devices Corp.) as follows.

Substrate (synthetic peptide capable of being phosphorylated by ROCK I or ROCK II: KEAKEKRQEQ-IAKRRRLSSLRASTSKSGGSQK) (SEQ ID NO:1) and ATP concentrations used were 200 nM and 10 µM, respectively, while the enzyme (ROCK I, ROCK II recombinantly-produced kinase domain) concentration was $3.96 \times 10^{-3}$ unitsper well. The substrate, enzyme, and ATP dilutions were made with reaction buffer provided by the vendor. The test compound was diluted in 1-:10 DMSO-ethanol (vol/vol). The various components were added into black, clear bottom 96-well plates in a final volume of 20 µL per well. After the enzyme reaction (60 min at 23° C.), 60 µL of the binding solution (IMA kits provided by vendor) was added per well and incubated an additional 30 min in the dark at 23° C. Fluorescent polarization of the reaction mixtures was then measured on the Analyst® HT instrument (Molecular Devices Corp.).

The data were analyzed using a non-linear interactive, sigmoidal-fit computer program from IDBS (Emeryville, Calif.) to generate inhibition constants for the test compound. $IC_{50}$ values (concentration of the drug to produce 50% inhibition of the enzyme activity) were obtained from multiple experiments.

The results are shown below in Table 1.

TABLE 1

|  | ROCK II $IC_{50}$ (µM) | ROCK I $IC_{50}$ (µM) | Selectivity for Rock II |
| --- | --- | --- | --- |
| Fasudil | 0.82 ± 0.04 | 2.1 ± 0.2 | No selectivity |
| BA-1049 | 1.6; 0.94 | 21; 21 | 13.1 -fold |

Data from table 1 are the mean ± standard deviation from 3-4 experiments for Fasudil. For BA-1049, results from two individual experiments are shown.

These results show that BA-1049 (racemic mixture) (Synthetica Fine Chemicals) has selectivity for ROCK II in contrast to Fasudil which is not selective for ROCK II.

Example 6

Effect of Fasudil and BA-1049 on the Endothelial Cell Actin Cytoskeleton

To determine the differential effects of Fasudil and BA-1049 (racemic mixture) on the endothelial actin cytoskeleton, HUVEC cells were studied.

For these experiments 20,000 HUVEC cells (ATTC, CRL-1730) were seeded in an 8 well collagen coated chamber slide, and treated with 0 (PBS), 10 µM or 25 µM BA-1049 (racemic mixture) (Synthetica Fine Chemicals), or with 10 µM or 25 µM Fasudil (Calbiochem). An adhesion of the cells was allowed from 16 hr to 24 hr prior to the start of incubation.

Cells were fixed with 10% formalin, permeabilized and incubated with Rhodamine-conjugated phalloidin (1/300) (Molecular Probes, Euchre, Oreg.) (R415). Actin was visualized under fluorescence using appropriate filter. Micrographs were taken at 400× magnification.

Figure 6C:
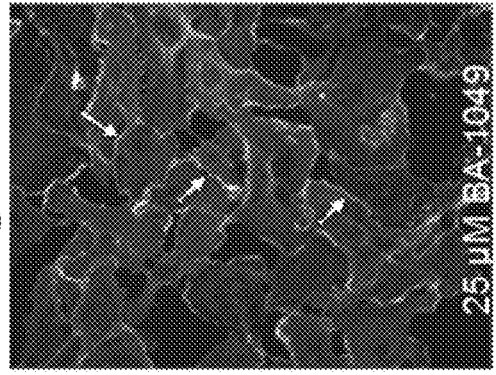
FIG. 6C is a representation of a fluorescence micrograph of HUVEC cells treated with 25 µM BA-1049 (racemic mixture), where the arrows point to actin at cell-cell junctions.
Figure 6B:
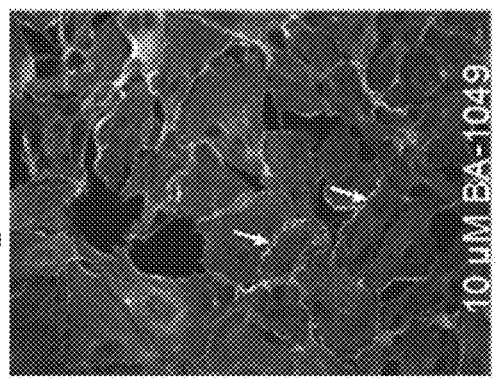
FIG. 6B is a representation of a fluorescence micrograph of HUVEC cells treated with 10 µM BA-1049 (racemic mixture), where the arrows point to actin at cell-cell junctions.
Figure 6E:
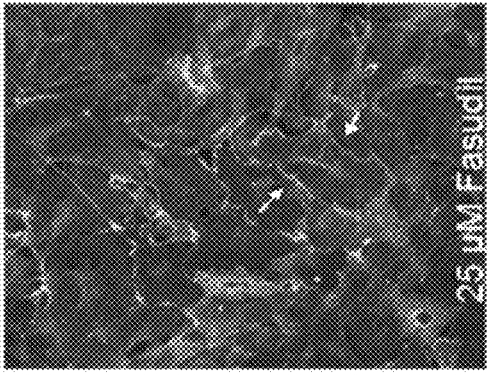
FIG. 6E is a representation of a fluorescence micrograph of HUVEC cells treated with 25 µM Fasudil, where the arrows point to actin at cell-cell junctions.
Figure 6D:
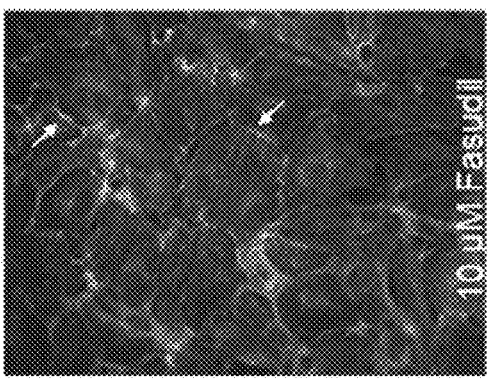
FIG. 6D is a representation of a fluorescence micrograph of HUVEC cells treated with 10 µM Fasudil, where the arrows point to actin at cell-cell junctions.
Figure 6A:
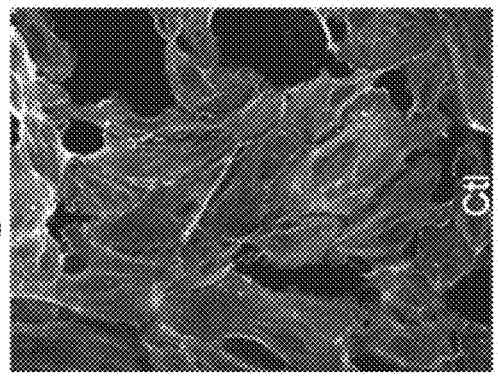
FIG. 6A is a representation of a fluorescence micrograph of HUVEC cells treated with saline (control (Ctl)), where the arrows point to actin at cell-cell junctions.

As shown in FIG. 6A, in control cells untreated with inhibitor, actin was distributed in long bundles of actin throughout the cells, the stress fibers, and is also concentrated at cell-cell junctions. Inhibition with BA-1049 disrupted stress fibers, and the actin at cell-cell junctions was clearly visible and the BA-1049 had little to no effect on junctional actin distribution (FIG. 6B and FIG. 6C). By contrast, Fasudil disrupted the peripheral actin to a greater extent than the stress fibers (FIG. 6D and FIG. 6E).

These results show that ROCK I and ROCK II disruption in endothelial cells has a differential effect, and that BA-1049 does not have the same cellular effect as Fasudil.

Example 7

Effect of BA-1049 and Fasudil on Cell-Cell Junctional Contact Proteins

To determine if BA-1049 (racemic mixture) and Fasudil differentially affect cell-cell junctional contact proteins, the following experiments were done.

HUVEC cells were cultured on collagen-I coated flasks in EGM-2 media (Clonetics, San Diego, Calif.) at 37° C. under a 5% $CO_2$ humidified atmosphere. They were divided and used for experiments (from passage 2 to 6) when they reached 80%-90% confluence. HUVEC cells were seeded onto 8-well chamber slides coated with collagen-I and allowed to adhere for 16-24 hr, and then treated with 10 μM or 50 μM BA-1049 (racemic mixture). Following incubation with the treatment agent, cells were either fixed in 10% formalin and then permeabilized for 30 min with 0.2% Triton X-100 (for actin and cadherin visualization), or were fixed for 5 min with 100% ice-cold MeOH (for occludin visualization). For actin staining, cells were blocked with 3% BSA for 45 min and then incubated for 1 hr at RT with Phalloidin conjugated to Rhodamine (1/300). For cadherin staining, fixed cells were blocked for 30 min with 10% goat serum, then incubated for 90 min at RT with mouse monoclonal pan-cadherin antibody (1/400). Detection was via FITC-conjugated goat anti-mouse IgG (1/400) for 1 hr at RT. For occludin staining, cells were fixed and blocked as for cadherin detection, then incubated for 120 min at RT with rabbit polyclonal occludin antibody (1/50). Detection was via FITC-conjugated goat anti-rabbit IgG (1/400). Slow-Fade® glycerol antifade (ThermoFisher Scientific) was used to decrease immunofluorescent fading. Slides were examined using an inverted fluorescence microscope (Carl Zeiss, West Germany). Micrographs were taken using Northern Eclipse Software (Empix Imaging, Inc., Mississauga, Ontario, Calif.).

Sub-confluent HUVEC (human umbilical vein endothelial cells) (American Type Culture Collection (ATCC), Manassas, Va.) (CRL-1730) were treated for 24 hr with PBS as control or with 50 μM Fasudil (Calbiochem) or BA-1049 (racemic mixture) (Synthetica Fine Chemicals). 20 μg of post-nuclear extracted proteins were loaded on a 7.5% SDS-PAGE gel and subjected to immunodetection with a specific cadherin antibody (Zymed Laboratories, San Francisco, Calif.) or occludin antibody (Zymed Laboratories). Erk antibody was used as loading control. Two independent series were analyzed in duplicate.

FIG. 7A reveals that cadherin increased significantly ($p<0.05$) by 1.2-fold following Fasudil or BA-1049 treatment. Occludin was significantly ($p<0.001$) decreased by 50% following Fasudil treatment (FIG. 7B), while BA-1049 produced a significant ($p<0.05$) increase of 1.3 fold. At a lower dose (25 μM), no significant effect was observed.

This result is consistent with the results from FIG. 6 showing that BA-1049 has a different effect than Fasudil on cell-cell contact regulation.

Example 8

Effect of BA-1049 and Fasudil on Endothelial Cell Tube Formation

To determine the effect of BA-1049 (racemic mixture) (Synthetica Fine Chemicals) and Fasudil (Calbiochem) on endothelial cell tube formation, an in vitro endothelial tubulogenesis assay system was used, which is composed of a microplate (96-wells) uniformly coated with extracellular matrix (ECMatrix™) (EMD Millipore Corporation, Billerica, Mass.). For these experiments, 15,000 HUVEC cells were seeded on ECMatrix™ with 10 μg/mL or 50 μg/mL or μM BA-1049 (racemic mixture) (Synthetica Fine Chemicals) or Fasudil and compared with untreated cells (Ctl). At the end of exposure, photographs were taken at 40× magnification (*A) and tube formation analyzed using Northern Eclipse image analysis software (Empix Imaging, Inc.). On extracellular matrix, endothelial cells rapidly align and form interconnecting networks that can display patent lumina. These structures are observable under phase contrast microscope after 6 hr to 8 hr and begin to deform after 24 hr.

Tube formation was observed in a range of time varying from 6 hr to 16 hr. At least 2 to 3 fields were taken for each condition and two independent experiments were quantified.

Figure 8B:
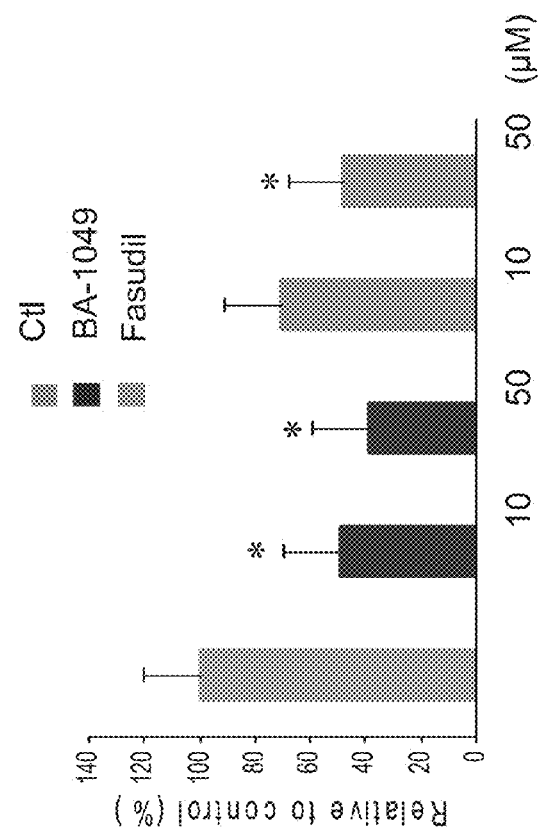
FIG. 8B is a graphic representation of the disruption of endothelial cell tube formation of treated cells relative to control.
Figure 8A:
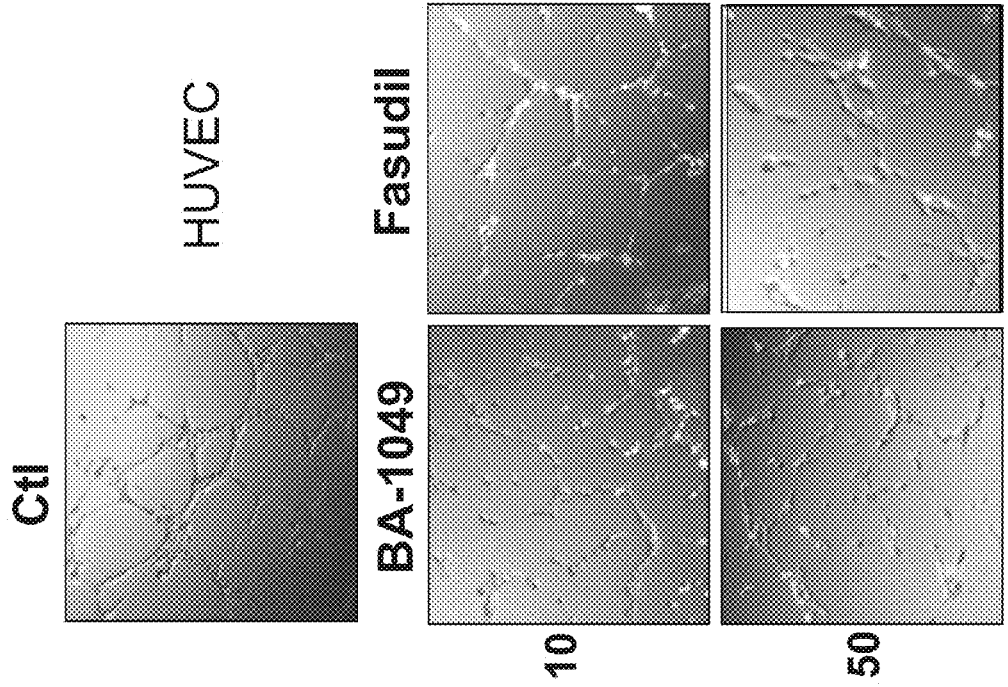
FIG. 8A is a photographic representation of a micrograph HUVEC cells treated with nothing (control (Ctl)), with 10 μM or 50 μM BA-1049 (racemic mixture), or with 10 μM or 50 μM Fasudil, where * shows treatment is statistically significant from control at $p<0.05$ (T-test)

As shown in FIG. 8A-FIG. 8B, control cells have well thick closed tubes with many connections compare to all the Rho kinase inhibitor treatments tested. The effect of BA-1049 (racemic mixture) and Fasudil on tube formation are comparable; some tubes are visible but are not always closed and are thin compared to untreated cells.

Example 9

Effect of BA-1049 and Fasudil on Endothelial Cell Proliferation

To determine the effect of BA-1049 (Synthetica Fine Chemicals) and Fasudil (Calbiochem) on endothelial cell proliferation, 2,000 HUVEC cells were incubated in F200 with large vessel endothelial supplement (ThermoFisher Scientific, Waltham, Mass.) (A1460901) for 4 hr, 24 hr, or 72 hr with 1 μM to 10 μM or μg/mL BA-1049 (racemic mixture) (Synthetica Fine Chemicals) or Fasudil. Cell proliferation was measured at 72 hr by using AlamarBlue® (ThermoFisher Scientific). At 4 hr and 24 hr, the media containing the test compounds was removed after the exposure and replaced with fresh media containing no tested compounds, and left in the incubator until the addition of AlamarBlue™. In some experiments, incubations of 72 hr were followed directly by staining with Alamar Blue™ dye. Fluorescence ($\lambda_{exc}$ 530 nm, $\lambda_{em}$ 590 nm) was measured with a SpectraMax Gemini EM spectrofluorometer (Molecular Devices Corp.) equipped with SoftmaxPro software (Molecular Devices Corp.). Student's t test statistical analyses were carried out using MicroSoft® Excel software (Microsoft Corp.)

Figure 9:
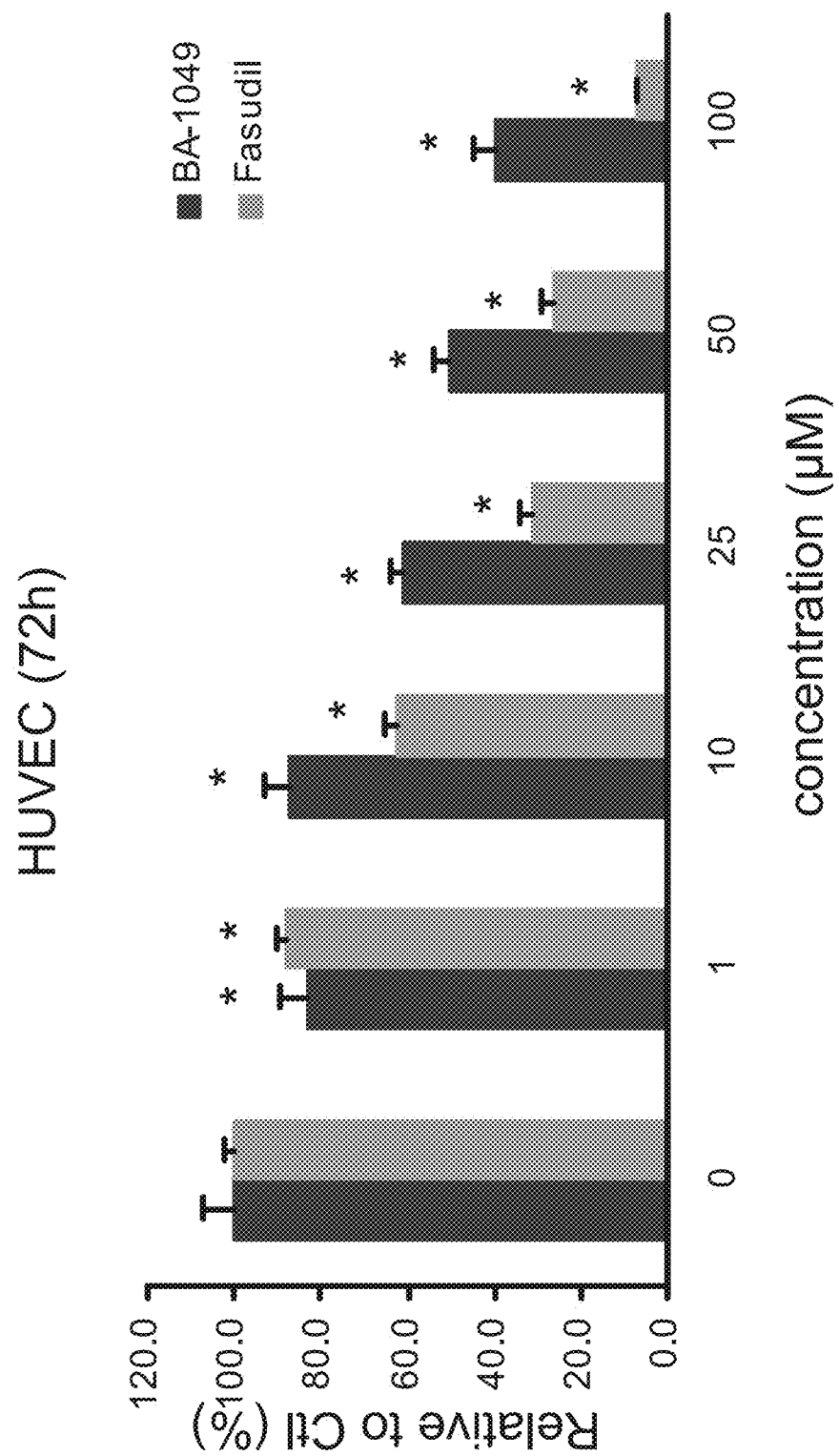
FIG. 9 is a graphic representation showing the effect of different concentrations of Fasudil and BA-1049 (racemic mixture) on HUVEC proliferation, where * reflects a p-value of <0.05;  reflects a p-value of <0.01; and * reflects a p-value of <0.001.

HUVEC cells were incubated as described above for 72 hr with concentrations varying from 1 μM to 100 μM or μg/mL of BA-1049 (racemic mixture) or Fasudil. Cell proliferation was measured by fluorescence using AlamarBlue® (ThermoFisher Scientific) at 72 hr. The results shown in FIG. 9 are presented as mean±s.d. for 2 independent experiments done.

These results show that a 72 hr incubation with either BA-1049 or Fasudil reduced proliferation of endothelial cells. The decrease ($p<0.05$ or $p<0.01$) in cell proliferation caused by BA-1049 or Fasudil appears at very low concentration (1 µM). BA-1049 did not disrupt proliferation to the same extent as Fasudil at a given concentration.

Example 10

Prediction of BA-1049 Toxicity Using in Silico Derek Nexus Screen

To indicate whether the chemical structure of BA-1049 qualitatively indicates a risk for toxicity, a DEREK-Nexus in silico screen (Lhasa Limited, Leeds, Yorkshire, UK) of the chemical structure was conducted. Derek Nexus screens provide toxicity predictions based on a knowledge-based software that can aid in the rejection of unsuitable drug candidates.

The Derek Nexus knowledge base (Derek KB 2014 1.0) is a software program that provides toxicity predictions based on knowledge rules and relationships derived from data on known structure-activity relationships in the field of toxicology. These data are collected from published sources and donated by member organizations; the data is collated, checked and verified by Lhasa scientists before use. Each rule/relationship is based on empirical observations supported by an understanding of toxicity mechanisms or by rigorous vetting processes. The goal is to permit an evaluation of the potential toxicological effects of a new compound by evaluating toxicological effects commonly associated with specific substructures or functional groups of the compound.

Derek Nexus knowledge rules and relationships based on structure-toxicity data from the following species were used during the screen for BA-1049: chicken, dog, E. coli, guinea pig, hamster, human, mammal, monkey, mouse, primate, rabbit, rat, rodent, Salmonella typhimurium, and bacteria in general. The Derek Nexus reasoning level was set to 'at least equivocal', indicating that there was an equal weight of evidence for and against a given proposition. The program was set to perceive tautomers and to show negative predictions. Rapid prototyping was permitted during the in silico evaluation of structure-toxicity data.

Table 2 contains a full summary of the 55 Derek Nexus toxicity endpoints on which BA-1049 toxicity was not indicated.

TABLE 2

Derek Nexus Endpoints Not Firing Toxicity Alerts for BA-1049 at Selected Reasoning Level

| | |
|---|---|
| Adrenal gland toxicity | Methaemoglobinaemia |
| alpha-2-mu-Globulin nephropathy | Mitochondrial dysfunction |
| Anaphylaxis | Mutagenicity in vivo |
| Bladder disorders | Nephrotoxicity |
| Bladder urothelial hyperplasia | Neurotoxicity |
| Blood in urine | Non-specific genotoxicity in vitro |
| Bone marrow toxicity | Non-specific genotoxicity in vivo |
| Bradycardia | Occupational asthma |
| Carcinogenicity | Ocular toxicity |
| Cardiotoxicity | Oestrogenicity |
| Cerebral oedema | Peroxisome proliferation |
| Chloracne | Phospholipidosis |
| Cholinesterase inhibition | Photo-induced chromosome damage in vitro |
| Chromosome damage in vivo | Photo-induced non-specific genotoxicity in vivo |
| Cumulative effect on white cell count and immunology | Photoallergenicity |
| Cyanide-type effects | Photocarcinogenicity |
| Developmental toxicity | Photomutagenicity in vitro |
| Hepatotoxicity | Pulmonary toxicity |
| HERG channel inhibition in vitro | Respiratory sensitisation |
| High acute toxicity | Skin sensitisation |
| Irritation (of the eye) | Splenotoxicity |
| Irritation (of the gastrointestinal tract) | Teratogenicity |
| Irritation (of the respiratory tract) | Testicular toxicity |
| Irritation (of the skin) | Thyroid toxicity |
| Kidney disorders | Uncoupler of oxidative phosphorylation |
| Kidney function-related toxicity | Urolithiasis |
| Lachrymation | |

No alerts for potential toxicity were raised on any of the 55 Derek Nexus toxicity endpoints, such as genotoxicity, mutagenicity or carcinogenicity. The only Derek Nexus alert identified for BA-1049 was Alert 508 for potential aryl sulfonamide-induced phototoxicity at the plausible prediction level. Several aryl sulphonamides have been shown to cause phototoxicity and photosensitization in various animal systems and in in vitro tests. A number of sulphonamide-containing pharmaceutical drugs have also been reported to cause photosensitization in humans. The strength of the phototoxicity response may be dependent on the method of administration.

These Derek Nexus results indicate that mutagenicity of BA-1049 in vitro in Salmonella typhimurium, Escherichia coli, and bacteria in general was inactive; no unclassified or misclassified features were present in BA-1049.

Example 11

Determination of Dose and Route of Administration of BA-1049

This study determines the most efficacious dose and route of administration that reduce Rho-kinase 2 (ROCK II) activation following transient MCAO-induced stroke in mice. This model rapidly detects BA-1049 (racemic mixture) efficacy in endothelial cells through the use of well characterized biomarkers for ROCK II activity, phosphorylated adducin (p-adducin), phosphorylated myosin light chain 2 (pMLC2), phosphorylated cofilin, phosphorylated LIMK1/2, and autophosphorylated ROCK II. Following efficacious route and dose selection, a time course is performed to assess the duration of the effect of BA-1049 (racemic mixture) based on duration of biomarker expression.

A. Animals and Dosing

The murine intraluminal monofilament model of middle cerebral artery occlusion (MCAO) is used in this study. MCAO involves the insertion of a surgical filament into the external carotid artery and threading it forward into the internal carotid artery until the tip occludes the origin of the MCA, resulting in a cessation of blood flow and subsequent brain infarction in the MCA territory. The technique is used herein to model transient occlusion. If the filament is removed after 1 h, reperfusion is achieved (transient MCAO).

Twenty 8 wk- to 9 wk-old C57BL/6 (Charles River Laboratories) were used in this study. For surgery, the mouse is placed in a supine position on an infrared heating pad. The fur over the ventral neck is shaved and the skin is disinfected with 70% ethanol and providone iodine. Under a stereo dissecting microscope, a 1 cm midline incision is made on the neck and retractors are used to expose the right common carotid artery (CCA), the external carotid artery (ECA) and the internal carotid artery (ICA). The arteries are carefully dissected to free them from surrounding nerves and fascia. The ECA is dissected further distally and two 8-0 silk sutures are tied around the ECA stump and a vascular clamp is applied at the bifurcation of the CCA into the ECA and ICA. A small incision is made at the end of ECA stump with Vannas-style spring scissors. A blunt 5-0 monofilament suture (Doccol) is inserted into the incision and advanced from the lumen of the ECA into the ICA for a distance of 9-10 mm beyond the bifurcation of CCA to occlude the origin of MCA. The inserted distance of the monofilament is critical, and for the mouse model a distance of 9-11 mm rostral to the CCA bifurcation will be inserted. After 60 min the monofilament is removed. The incision is sutured with 4.0 prolene sutures. Inject 1 mL saline subcutaneously and 0.1 mg/kg buprenorphine subcutaneously every 8 hr to 12 hr for up to 48 hr to decrease pain, and allow to recovery. Mice are maintained on an infrared heating pad until thermoregulation is re-established.

The test article dosing solutions are prepared by dissolving BA-1049 (racemic mixture) (Synthetica Fine Chemicals) powder in sterile PBS in order to achieve concentrations of 10 mg/mL, 25 mg/mL, and 50 mg/mL for groups B, C, and D, respectively. The pH of test article dosing solutions is adjusted to 7. After preparation, the dosing solutions are kept on ice until use, retained dosing solutions will be stored at −20° C.

The test article dosing solutions are prepared by dissolving Fasudil (Calbiochem) powder in sterile PBS in order to achieve concentrations of 10 mg/mL, 25 mg/mL, and 50 mg/mL for groups B, C, and D, respectively. The pH of test article dosing solutions will be adjusted to 7. After preparation, the dosing solutions are kept on ice until use, retained dosing solutions are stored at −20° C.

Assuming that the maximal weight of a mouse on the treatment day is 20 g, the calculation for the amount of BA-1049 needed for each group of mice at the proposed doses is performed in Table 3 below.

TABLE 3*

| Treatment Group | Total number of mice | Body weight (g) | Dose (mg/kg) | Amount of BA-1049 (mg) needed for 1 mouse | Amount of BA-1049 (mg) needed for 5 mice | Volume of PBS (mL) needed to dissolve BA-1049 (0.2 mL/mouse) | Concentration of BA-1049 (mg/mL) |
|---|---|---|---|---|---|---|---|
| A | 4 | 20 | 0 | 0 | 0 | 1 | 0 |
| B | 4 | 20 | 10 | 0.2 | 1.0 | 1 | 1.0 |
| C | 4 | 20 | 25 | 0.5 | 2.5 | 1 | 2.5 |
| D | 4 | 20 | 50 | 1.0 | 5.0 | 1 | 5.0 |

*An additional animal is added to account for dead volume loss.

Assuming that the maximal weight of a mouse on the treatment day is 20 g, the calculation for the amount of Fasudil needed for each group of mice at the proposed doses is performed in Table 4 below:

TABLE 4

| Treatment Group | Total number of mice | Body weight (g) | Dose (mg/kg) | Amount of Fasudil (mg) needed for 1 mouse | Amount of Fasudil (mg) needed for 5 mice | Volume of PBS (mL) needed to dissolve Fasudil (0.2 mL/mouse) | Concentration of Fasudil (mg/mL) |
|---|---|---|---|---|---|---|---|
| A | 4 | 20 | 0 | 0 | 0 | 1 | 0 |
| B | 4 | 20 | 10 | 0.2 | 1.0 | 1 | 1.0 |
| C | 4 | 20 | 25 | 0.5 | 2.5 | 1 | 2.5 |
| D | 4 | 20 | 50 | 1.0 | 5.0 | 1 | 5.0 |

The study consists of 3 parts as follows in Tables 5 through 9.

TABLE 5

Part 1: Practice MCAO on control mice to pilot WB and IHC techniques

| Group | N | Surgical Procedure | Sample |
|---|---|---|---|
| 1 | 4 | Transient (60 min.) MCAO | Lysate |
| 2 | 4 | Transient (60 min.) MCAO | OCT Block |

TABLE 6

Part 2: Determination of an efficacious dose of BA-1049 vs. Fasudil, intraperitoneal (IP) inj.

| Group | N | Surgical Procedure | Route | Treatment, Dose |
|---|---|---|---|---|
| 1 | 4 | Transient (60 min.) MCAO | IP | PBS |
| 2 | 4 | Transient (60 min.) MCAO | IP | BA-1049 (racemate), 10 mg/kg |
| 5 | 4 | Transient (60 min.) MCAO | IP | Fasudil, 10 mg/kg |

TABLE 7

Part 3a: Determination of optimal delivery method, IP vs. Oral Gavage (PO)

| Group | N | Surgical Procedure | Route | Treatment, Dose |
|---|---|---|---|---|
| 1 | 4 | Transient (60 min.) MCAO | IP | BA-1049 (racemate), 10 mg/kg |
| 2 | 4 | Transient (60 min.) MCAO | PO | BA-1049 (racemate), 10 mg/kg |
| 3 | 4 | Transient (60 min.) MCAO | PO | BA-1049 (racemate), 25 mg/kg |
| 4 | 4 | Transient (60 min.) MCAO | PO | BA-1049 (racemate), 50 mg/kg |

TABLE 8

Part 3b: Determination of optimal delivery method, IP vs. SC

| Group | N | Surgical Procedure | Route | Treatment, Dose |
|---|---|---|---|---|
| 1 | 4 | Transient (60 min.) MCAO | IP | BA-1049 (racemate), 10 mg/kg |
| 4 | 4 | Transient (60 min.) MCAO | SC | BA-1049 (racemate), 10 mg/kg |
| 5 | 4 | Transient (60 min.) MCAO | SC | BA-1049 (racemate), 25 mg/kg |
| 6 | 4 | Transient (60 min.) MCAO | SC | BA-1049 (racemate), 50 mg/kg |

TABLE 9

Part 4: Time course of BA-1049 efficacy following selection of best route and dose

| Group | N | Surgical Procedure | Route | Treatment, Dose | Collection post-MCAO |
|---|---|---|---|---|---|
| Dose and perform MCAO surgery on Groups 1-3 | | | | | |
| 1 | 4 | Transient (60 min.) MCAO | TBD | BA-1049 (racemate), TBD mg/kg | 1 d |
| 2 | 4 | Transient (60 min.) MCAO | TBD | BA-1049 (racemate), TBD mg/kg | 2 d |
| 3 | 4 | Transient (60 min.) MCAO | TBD | BA-1049(racemate), TBD mg/kg | 3 d |
| Analyze Groups 1-3, if biomarkers persist dose and perform MCAO surgery on Group 4 | | | | | |
| 4 | 4 | Transient (60 min.) MCAO | TBD | BA-1049 (racemate), TBD mg/kg | 7 d |
| Analyze Group 4, if biomarkers persist dose and perform MCAO surgery on Group 5 | | | | | |
| 5 | 4 | Transient (60 min.) MCAO | TBD | BA-1049 (racemate), TBD mg/kg | 12 d |

For Part 2 (see #1, Study Design, above), the test and vehicle articles are administered at the specified dose at a volume of about 0.2 mL (actual volume is adjusted based on individual body weights) to all mice as a single dose i.p. 30 min prior to MCAO surgery using sterile 1 mL-syringes fitted with a 25 G ⅝ needle.

For Part 3a/3b, the test and vehicle articles are administered at the specified dose at a volume of about 0.2 mL (actual volume is adjusted based on individual body weights) g to all mice by either oral gavage (PO) (<10 mg/kg) 30 min prior to MCAO surgery (3a) or subcutaneous (SC) injection in the right flank 30 min prior to MCAO surgery (3b) on the treatment day using sterile 1 mL-syringes fitted with a 25 G ⅝ needle.

At 24 hr post-MCAO surgery, mice are euthanized and brains collected for biomarker analysis by Western Blot analysis or Immunohistochemistry. For Western Blot analysis, mice are anesthetized using isoflurane and perfused intracardially using normal saline (0.9% NaCl). The right and left middle cerebral arteries supply the lateral surface of their respective lobes in the territory of the motor and sensory cortices. The brain rostral to the cerebellum (excluding olfactory bulb) is collected ipsilateral (right hemisphere) and contralateral (left hemisphere) to the occlusion. Ipsilateral and contralateral hemispheres are collected in 2 separate tubes. Brain weights are recorded in both the "Ipsilateral and Contralateral Mouse Brain Collection Checklists." Frozen brain tissue are further processed into tissue lysates following the experimental protocol documented below.

For Immunohistochemistry, mice are anesthetized using isoflurane and perfused intracardially using paraformaldehyde (4% PFA). Brain weights are recorded in "IHC Mouse Brain Collection Checklist."

Brain specimens from fixed animals are frozen in OCT and sectioned.

B. Tissue Lysate Preparation and Quantification 20 uL protease inhibitor (Halt, Protease, Fischer Scientific) and 10 μL phosphatase inhibitor (Fischer Scientific) are added to 1 mL RIPA buffer (Santa Cruz Biotechnology, Inc.). 0.5 mL lysis buffer is added to each tissue sample and the tissues ground individually using a clean BioMasher II® tube/pestle (Kimble Chase Life Science, Vineland, N.J.) for each sample. The mixture is vortexed to aid in tissue lysis and centrifuged at 4° C. for 10 min at 13,000 rpm. The supernatants from each tube are collected. The protein concentration of each sample is determined using the DC Protein Assay Kit and following the manufacturer's instructions.

C. Immunoblotting

Protein lysates are analyzed by Western Blot analysis following the experimental protocol below in Table 10.

TABLE 10

| Primary Antibody | Dilution | Secondary Antibody | Dilution |
|---|---|---|---|
| pCofilin rabbit polyclonal (Cell Signaling Cat# 3313, lot# 7) | 1:500 | Anti-Rabbit IgG HRP (Cell Signaling Cat# 7074, lot #26) | 1:1500 |
| pROCK II rabbit polyclonal (Genetex Cat# GTX122651, lot# 42025) | 1:500 | Anti-Rabbit IgG HRP (Cell Signaling Cat# 7074, lot #26) | 1:1500 |
| Cyclophilin 40 rabbit polyclonal (Santa Cruz Cat# sc-66848, lot# H3103) | 1:2000 | Anti-Rabbit IgG HRP (Cell Signaling Cat# 7074, lot #26) | 1:1500 |
| pMLC2 (Thr18/Ser19) rabbit polyclonal (Cell Signaling Cat#3674, lot# 3) | 1:1000 | Anti-Rabbit IgG HRP (Cell Signaling Cat# 7074, lot #26) | 1:1500 |
| pMLC2 (Ser19) rabbit polyclonal (Cell Signaling Cat#3671, lot# 3) | 1:500 | Anti-Rabbit IgG HRP (Cell Signaling Cat# 7074, lot #26) | 1:1500 |
| pAdducin Rabbit polyclonal (Santa Cruz Cat# sc-16738, lot# B0414) | 1:200 | Anti-Rabbit IgG HRP (Cell Signaling Cat# 7074, lot #26) | 1:1500 |
| pLIMK1/2 rabbit polyclonal (Cell Signaling Cat#3841, lot# 6) | 1:500 | Anti-Rabbit IgG HRP (Cell Signaling Cat# 7074, lot #26) | 1:1500 |

D. Immunohistochemistry

Frozen tissue sections embedded in OCT are analyzed by immunohistochemistry using the antibodies described in Table 11.

TABLE 11

| Primary Antibody | Dilution | Secondary Antibody | Dilution |
|---|---|---|---|
| pCofilin rabbit polyclonal (Cell Signaling Cat# 3313, lot# 7) | 1:100 | Alexa 488 Anti-Rabbit IgG (Molecular Probes Cat# A11008, lot #1622775) | 1:500 |
| Von Willibrand's Factor rabbit polyclonal (Millipore Cat#AB7356, Lot# XXX) | 1:250 | Alexa 488 Anti-Rabbit IgG (Molecular Probes Cat# A11008, lot #1622775) | 1:500 |
| pMLC2 (Thr18/Ser19) rabbit polyclonal (Cell Signaling Cat#3674, lot# 3) | 1:250 | Alexa 488 Anti-Rabbit IgG (Molecular Probes Cat# A11008, lot #1622775) | 1:500 |
| pMLC2 (Ser19) rabbit polyclonal (Cell Signaling Cat#3671, lot# 3) | 1:100 | Alexa 488 Anti-Rabbit IgG (Molecular Probes Cat# A11008, lot #1622775) | 1:500 |
| pAdducin rabbit polyclonal (Santa Cruz Cat# sc-16738, lot# B0414) | 1:250 | Alexa 488 Anti-Rabbit IgG (Molecular Probes Cat# A11008, lot #1622775) | 1:500 |

Biomarker levels in normal control and ischemic brain lysates on Western blots are quantitated by band densitometry using Alpha Imager software. Results are presented as mean±SEM.

Example 12

Safety and Toxicity of BA-1049 (R) In Vivo

A. Maximum Tolerated Dose

BA-1049 (R enantiomer) is introduced into BALB/c mice (Charles River Laboratories, Wilmington, Mass.) intravenously or by oral gavage according to the body weight at a starting dose of 1 mg/kg. The mice are continually monitored for acute signs of toxicity (behavior, movement, diarrhea) for the first 2 hr, and if required, are sacrificed by $CO_2$ asphyxiation followed by necropsies. Increased doses (e.g., up to 100 mg/kg) are administered if body weight loss is less than 15% after 2 d following the administration. All mice are monitored daily for signs of toxicity for 14 d and body weights are measured 3 times a wk at regular intervals during the study.

These studies establish a maximum tolerated dose (MTD) for the oral and intravenous administration for BA-1049 (R). MTD is defined as the highest dose given that does not lead to death or produce a moribund state while maintaining body weight loss within 15%.

B. Tolerability of Repeat Administration

BALB/c mice are randomly distributed into groups of placebo, low, medium, and high dose (4 females and 4 males per group). Mice are administered BA-1049 (R) at 0 mg/kg, 1 mg/kg, 5 mg/kg, or 10 mg/kg daily (the highest dose as determined by the MTD) for 3 wk by 2 routes of administration: oral gavage and subcutaneously. The mice are monitored for their health status. The weight, fur, skin, food and water intake and overall health of mice is monitored in treated vs. untreated groups. At 3 wk the animals are euthanized and subject to post-mortem examination. The gross morphology and pathology of organ systems is examined. Samples of brain and brain endothelial cells (taken from the subventricular zone) are taken for analysis of the concentration of BA-1049 by LCMS. Various organs are sectioned and stained for H&E and histopathology is determined for the different dose groups and routes of administration.

These studies establish the level of systemic toxicity of BA-1049 (R) when administered as a repeated dose in mice by oral gavage or subcutaneously.

Example 13

PK Study Evaluating Routes of BA-1049 (R) Administration In Vivo

To determine the plasma concentrations and pharmacokinetics of BA-1049 (R) following a single intravenous (IV) (5 mg/kg), intraperitoneal (IP) (10 mg/kg), or oral dose (PO) (30 mg/kg) administration to C57BL/6 male mice, the following testing was done in C57BL/6 mice (Charles River Laboratories) 8 wk to 10 wk old (Table 12).

TABLE 12

| Route | To deliver | Volume | Concentration of dosing solution | Volume of PBS needed | Weight of TA in vial |
|---|---|---|---|---|---|
| IV | 0.125 mg | 0.1 mL | 1.25 mg/mL | 3 mL | 3.75 mg |
| IP | 0.25 mg | 0.5 mL | 0.5 mg/mL | 15 mL | 7.5 mg |
| PO | 0.75 mg | 0.2 mL | 3.75 mg/mL | 6 mL | 22.5 mg |

The test drug, BA-1049 (R) is provided as described in Table 13 below:

TABLE 13

| Group # | No. of Mice/Sex | Route of Administration | Dose (mg/kg) | Dose Conc. (mg/mL) | Dose Vol. (mL/kg) | Dose Vol. (µL/g) |
|---|---|---|---|---|---|---|
| 1 | 24M | IV | 5 | 1.25 | 4.0 | 4 |
| 2 | 24M | IP | 10 | 0.5 | 20.0 | 20 |
| 3 | 24M | PO | 30 | 3.75 | 8.0 | 8 |
| 4* | 5M | — | — | — | — | — |

*Group 4 is for collection of naïve whole brain only and will not be dosed.

BA-1049 (R) is provided once as follows: Each IV dosing syringe is weighed loaded and unloaded to at least 4 decimal places. The actual dose (5 mg/Kg) administered to the animal is the difference between the loaded and unloaded dosing syringe weights. Each IP dosing syringe is weighed loaded and unloaded to at least 4 decimal places. The actual dose (10 mg/Kg) administered to the animal is the difference between the loaded and unloaded dosing syringe weights. 30 mg/Kg PO administration is conducted using a ball-tipped, stainless steel gavage needle attached to a plastic syringe.

A. Pharmacokinetics

Following IV dose administration, terminal blood samples (about 1 ml-2 ml each) are collected from 4 animals at each of the following timepoints post-dose: 0.083 hr, 0.5 hr, 2 hr, 6 hr, 12 hr, and 24 hr. Following IP or PO dose administration, terminal blood samples (about 1 ml-2 ml each) are collected from 4 animals at each of the following timepoints post-dose per dose route: 0.25 hr, 1 hr, 4 hr, 8 hr, 12 hr, and 24 hr. Each animal is anesthetized by $CO_2$ inhalation and terminal blood samples are collected via cardiocentesis and transferred into pre-labeled tubes containing sodium heparin as the anticoagulant. Following cardiocentesis blood collection, the animal is returned to the $CO_2$ chamber and euthanized by $CO_2$ asphyxiation. Collected blood samples are gently inverted several times to mix the anticoagulant. Blood samples are centrifuged at about 3000×g rpm for 10 min at about 4° C., [resultant plasma is observed for hemolysis]. All derived plasma samples are stored frozen at approximately −80° C. until further processing.

B. Brain Harvesting

Following IV dose administration, whole brain is collected following cardiocentesis from 4 animals at each of the following time points post-dose: 0.083 hr, 0.5 hr, 2 hr, 6 hr, 12 hr, and 24 hr. Following IP and PO dose administration, whole brain is collected following cardiocentesis from 4 animals at each of the following time points post-dose per dose route: 0.25 hr, 1 hr, 4 hr, 8 hr, 12 hr, and 24 hr. Whole brain is rinsed in 1×PBS, the tissue weight recorded and snap frozen in pre-labeled tubes using liquid nitrogen. In addition, whole brain from 5 naïve mice is harvested at 24 hr, rinsed in 1×PBS, the tissue weight recorded and snap frozen in pre-labeled tubes using liquid nitrogen.

C. Bioanalytical Analysis

Samples are analyzed by LC-MS/MS using an Agilent 6410 mass spectrometer coupled with an Agilent 1200 HPLC and a CTC PAL chilled autosampler, all controlled by MassHunter software (Agilent, Lexington, Mass.). After separation on an X-Select HPLC column (Waters, 130A, 3.5 µm, 2.1×50 mm) using an acetonitrile-water gradient system (shown below), peaks were analyzed by mass spectrometry (MS) using ESI ionization in MRM mode.

For calibration samples, a working dilution of the test article at 25 times the final concentration is prepared and serially diluted (3-fold). These samples are diluted 25-fold into C57BL/6 mouse blank plasma and mixed with three volumes of acetonitrile containing an analytical internal standard (propranolol), incubated on ice for 10 min at 4° C. and then centrifuged. The protein-free supernatant is used for LC-MS/MS analysis.

Example 14

Mouse Models of CCM

Rho kinase inhibitors with the most promising in vitro data (obtained in Example 2) are evaluated in mouse models of CCM. Mouse models can be used to mimic CCM pathology in human subjects with primary mutations in Ccm genes. These models consist of mice heterozygous for a targeted loss-of-function mutation in one of the Ccm genes (first hit) in a background of elevated random somatic mutations (second hit, homozygous knockout of Msh2 component of mismatch repair complex). As primary Ccm1 or Ccm3 mutations form the basis for the majority (80%-90%) of inherited disorders in most populations, Ccm1 and Ccm3 mouse models are used in this study. The following mouse lines are generated as follows:

A Ccm1+/−; A starting Ccm1+/− mouse line is generated using a targeted loss of function mutation. This is accomplished by transfecting R1 embryonic stem cells with a vector including a construct designed to delete the first ankyrin repeat of Ccm 1 and screening for a founder transmitting the mutant allele to its progeny. Mice heterozygous for the allele are backcrossed to C57BL/6J mice to ensure background purity.

A Msh2+/−: An Msh2 knockout line is generated by crossing mice with an allele of Msh2 flanked by loxP sites with a strain containing the Cre recombinase transgene under EIIa promoter control (B6.FVB-Tg(EIIa-cre) C5379Lmgd/J). Mice are then back-crossed to C57BL/6J to breed out the Cre transgene.

A CCM1+/−Msh2−/−: A three-generation cross is used to produce CCM1+/−Msh2−/− mice from the lines generated in steps (1) and (2). First, Msh2+/− animals are crossed with Ccm1+/− mice to produce double heterozygous mice (CCM1+/−Msh2+/−). The double heterozygous mice are then intercrossed to generate CCM1+/−Msh2−/− mice. The mouse line is back-crossed with C57BL/6J mice for at least 12 generations to ensure the purity of the background strain.

Example 15

Reduction of Future CCM Lesion Burden In Vivo

The following experiment tests the efficacy of test Rho kinase inhibitors (as determined in Example 2) as prophylactic treatments to reduce lesion burden in vivo in various mouse models of CCM created in Example 15.

Ten P21 Ccm1+/−Msh2−/− and Ccm3+/−Msh2−/− mice are randomly assigned to each of the 3 test groups: (1) BA-1049 (R) (NuChem Therapeutics); (2) Fasudil (Calbiochem); and (3) Control.

Half of the mice in each test group (5 animals/group) receive daily doses of the test article/control (see Table 14) dissolved in 4 mL drinking water from the time of randomization to 5 mos of age. Daily doses are selected based on the most promising doses in in vitro studies (Section 1.0). The control group receives a buffer vehicle. The other half of the mice in each test group (5 animals/group) receive weekly doses of the test article/control dissolved in 4 mL drinking water from the time of randomization to 5 mos of age. Weekly doses are selected based on the most promising doses in in vitro studies (Section 1.0). The control group receives a buffer vehicle (see Table 14).

TABLE 14

| Example: CCM Prophylactic | Number of Ccm1 Mice | | Number of Ccm3 Mice | | Total |
|---|---|---|---|---|---|
| | Daily Dose | Weekly Dose | Daily Dose | Weekly Dose | |
| BA-1049 (R) | 5 | 5 | 5 | 5 | 20 |
| Fasudil | 5 | 5 | 5 | 5 | 20 |
| Control | 5 | 5 | 5 | 5 | 20 |
| Total Mice | | | | | 60 |

All mice are weighed immediately prior to dosing, to ensure an accurate calculation of the appropriate dose necessary to achieve the desired final concentration. At the end of the 24-hr period following a given dose, drinking water containers are monitored to ensure consumption of the full 4 mL (and so full test article dose).

At 5 mos of age, each mouse is euthanized by $CO_2$ asphyxiation. Following euthanasia, the brain of each mouse is removed and fixed in 10% formalin for 2 wk. Each brain is labeled with an identification number to permit future blinded analysis.

The prevalence and characteristics of CCM lesions in collected brains are analyzed by individuals blinded to the original dosing regimen, treatment group, and model. Quantitative results for each analysis endpoint are calculated by 2 independent individuals and subsequently averaged. The following sections discuss data collection and analysis for each endpoint used in lesion assessment.

The total number of CCM lesions in each brain is identified by high-field MRI with a 14.1 T (600 MHz) imaging spectrometer. For this analysis, 3D-gradient recalled (GRE) images are acquired with a slice thickness of 250 μM, in-plane pixel size of 113 μM, repetition time (TR) of 100 ms, and echo time (TE) of 10 ms. Lesions are identified and counted by independent, blinded assessors.

MRI-based quantification of CCM lesion count is complemented by a histological analysis of the number of lesions in coronal slices. For this analysis, brains are cut into 14 1 mm thick coronal slices, from the olfactory bulbs at the frontal rostrum to the most caudal portion of the cerebellar hindbrain. Each slice is embedded in paraffin, sliced into 5 μM thick sections with a microtome, mounted onto charged microscope slides for hematoxylin and eosin staining, and then examined by independent assessors for lesion identification and counting.

The maximal cross-sectional diameter of each lesion (lesion size) is quantified based on analysis of MRI slices. The maximal cross-sectional area of each lesion (area/lesion), as well as the sum of the maximal cross-sectional areas of all lesions in a given animal (lesion area/brain) are also quantified.

To complement the MRI-based lesion analysis, mounted histological sections are analyzed by independent assessors to determine the maximal cross-sectional diameter of each lesion (lesion size), the maximal cross-sectional area of each lesion (area/lesion), and the sum of the maximal cross-sectional areas of all lesions in a given animal (lesion area/brain).

Mounted histological sections are analyzed to determine the number of Stage 1 vs Stage 2 lesions per brain and the proportion of Stage 2 lesions per brain. A Stage 1 CCM lesion is defined as an isolated, dilated capillary with a width of at least 25 red blood cells (a 'cavern') and a Stage 2 lesion is defined as a cluster of 2 or more contiguous caverns.

Perls' Prussian stain (Leica Biosystems, Buffalo Grove, Ill.) is used to assess iron deposits in the area surrounding a lesion, as a marker of lesion blood leakage and so lesion severity. Individual brain slices are treated with 30% hydrochloric acid and 10% potassium ferocyanide and counterstained with nuclear fast red. The number of Prussian blue iron deposits per lesion and proportion of lesions per brain with iron deposits is quantified.

Slices adjacent to those used in iron deposit analyses are stained by immunochemistry using primary antibodies for macrophages (mouse monoclonal anti-CD11b) (eBioscience, San Diego, Calif.) (14-0112-81), B cells (mouse monoclonal anti-B220 (BD Biosciences, San Jose, Calif.) (550286), plasma cells (mouse monoclonal anti-CD138 (BD Biosciences) (553712), and a biotinylated secondary antibody (Vector Laboratories, Burlingame Calif.) (BA 4000). The number of each type of inflammatory cell per cavern is evaluated for each lesion and for the brain as a whole (a higher inflammatory response is associated with more severe lesions).

Slices stained for immunochemical analyses are also labeled for proliferation-associated nuclear protein Ki-67 (mouse monoclonal anti-Ki67 antibody (DAKO, Carpinteria, Calif.) (M7249). The relative proliferation of endothelial cells (EC) is quantified by calculating an EC proliferative index (the ratio of Ki67-immunopositive EC/total number of EC lining a given cavern) for each lesion and for the brain as a whole.

To assess relative levels of Rho kinase activity in lesion endothelial cells, immunochemical slices are also stained for phosphorylated myosin light chain (pMLC, rabbit polyclonal anti-pMLC) and phosphorylated myosin basic subunit (pMBS, rabbit polyclonal anti-pMBS) (Cell Signaling Technology, Danvers, Mass.) (2634, 3671). Immunostaining of endothelial cells lining each cavern is characterized as absent, weak, or strong and the proportion of 'absent' caverns and proportion of 'strong' caverns is calculated for each brain.

B. Results

Treatment with BA-1049 (R) or Fasudil reduces the total number of lesions, reduces average lesion size and area, reduces the prevalence and proportion of stage 2 lesions, reduces the number of iron deposits near a given lesion, reduces the level of inflammatory invasion in a given cavern, reduces the endothelial cell proliferative index, and reduces Rho kinase activity in lesion endothelial cells, in comparison with control mice.

These results demonstrate that individuals heterozygous for Ccm1 and Ccm3 mutations due to inheritance of autosomal dominant mutation in gene and individuals with an identified spontaneous lesion who are thus at a risk for future lesion development can be prophylactically treated with pharmaceutical formulations with BA-1049 (R) or Fasudil.

Example 16

Reduction of Prevalence/Size of Existing CCM Lesions In Vivo

Various Rho kinase inhibitors are tested for their efficacy as a treatment to reduce the size of existing lesions in vivo or to eliminate these lesions from the vasculature in vivo.

A. Procedures

All mice undergo baseline in vivo high-field MRI with a 14.1 T (600 MHz) imaging spectrometer at 3 mos of age. During this imaging, 3D-gradient recalled (GRE) images are acquired with a slice thickness of 250 μM, in-plane pixel size of 113 μM, repetition time (TR) of 100 ms, and echo time (TE) of 10 ms. All image sets are labeled with identification numbers to permit blinded analysis.

Half of the mice in each test group (10 animals/group) receive daily doses of the test article/control dissolved in 4 mL drinking water from 3 mos of age (immediately following baseline imaging) to 6 mos of age. Daily doses selected based on in vitro test results (Section 1.0). The control group receives a buffer vehicle. The other half of the mice in each test group (10 animals/group) receive weekly doses of the test article/control dissolved in 4 mL drinking water from 3 mos of age (immediately following baseline imaging) to 6 mos of age. Weekly doses are selected based on in vitro test results. The control group receives a buffer vehicle. These results are summarized in Table 15.

All mice are weighed immediately prior to dosing, to ensure an accurate calculation of the appropriate dose necessary to achieve the desired final concentration. At the end of the 24 hr period following a given dose, drinking water containers are monitored to ensure consumption of the full 4 mL (and so full test article dose). At 6 mos of age, all mice undergo in vivo high-field MRI using the procedures described above for the baseline, 3 mo assessment.

At the time of 6 mo imaging, animals in each dose regimen in each treatment group are divided into 2 cohorts. Cohort 1 includes half of the animals receiving daily doses in each treatment group (5/10 animals)+half of the animals receiving weekly doses in each treatment group (5/10 animals). Cohort 1 is used for histological analyses of control vs treated lesions at 6 mos. Cohort 2 includes the remaining half of the animals receiving daily doses in each treatment group (5 animals)+the remaining half of the animals receiving weekly doses in each treatment group (5 animals). Cohort 2 is used to assess whether a treatment effect visible at 6 mos of age is still apparent at 9 mos of age.

Immediately following 6 mo imaging, Cohort 1 is euthanized by $CO_2$ asphyxiation. The brain of each euthanized mouse is removed and fixed in 10% formalin for 2 wk. Each brain is labeled with an identification number to permit future blinded analysis.

At 9 mos of age, Cohort 2 undergoes in vivo high-field MRI using the procedures described above for the baseline, 3 mo assessment. Immediately following 9 mo imaging, Cohort 2 is euthanized by $CO_2$ asphyxiation. The brain of each euthanized mouse is removed and fixed in 10% formalin for 2 wk. Each brain is labeled with an identification number to permit future blinded analysis.

MRI slices are used to determine the change in lesion number and lesion size (area, diameter) from baseline to 6 mos of age in each mouse. For this analysis, the total number of lesions, maximal cross-sectional diameter of each lesion, maximal cross-sectional area of each lesion (area/lesion), and sum of the maximal cross-sectional areas of all lesions in a given animal (lesion area/brain) are quantified at baseline and at 6 mos. The changes from baseline to 6 mos in each category are calculated.

To analyze whether decreases in lesion diameter/area/number are maintained after completion of the dosing regimen, the 9 mo images from Cohort 2 are analyzed to permit a similar quantification of total lesion number, lesion diameter, area/lesion, and lesion area/brain. Change from baseline to 9 mos in each category is quantified and compared with the change from baseline to 6 mos. Change from 6 mos to 9 mos in each category is also quantified.

As described above in Example 16, quantitative results for each analysis endpoint are calculated by two independent, blinded individuals and subsequently averaged.

TABLE 15

| CCM Treatment With | Cohort 1[b] | Cohort 2 | Cohort 1 | Cohort 2 | Cohort 1 | Cohort 2 | Cohort 1 | Cohort 2 | |
|---|---|---|---|---|---|---|---|---|---|
| BA-1049 (R) | 5 | 5 | 5 | 5 | 5 | 5 | 5 | 5 | 40 |
| BA-1049 (R) + Fasudil | 5 | 5 | 5 | 5 | 5 | 5 | 5 | 5 | 40 |
| Fasudil | 5 | 5 | 5 | 5 | 5 | 5 | 5 | 5 | 40 |
| Control | 5 | 5 | 5 | 5 | 5 | 5 | 5 | 5 | 40 |
| Total Mice | | | | | | | | | 160 |

[b]Cohort 1 is euthanized for analysis at 6 mos of age; Cohort 2 is imaged and then euthanized at 9 mos of age MRI-based primary analyses are complemented by histological analyses of control vs treated Cohort 1 mouse brains collected at 6 mos of age. To analyze whether changes from control last beyond cessation of treatment, Cohort 2 mouse brains collected at 9 mos of age are similarly analyzed.

For this analysis, brains are cut into 14 1 mm thick coronal slices, from the olfactory bulbs at the frontal rostrum to the most caudal portion of the cerebellar hindbrain. Each slice is embedded in paraffin, sliced into 5 μM thick sections with a microtome, mounted onto charged microscope slides for hematoxylin and eosin staining, and then examined by two independent, blinded assessors.

Coronal sections are analyzed as described above to assess the same endpoints described in Example 16: (1) the total number of lesions; (2) lesion size; (3) lesion stage; (4) iron deposits near lesion, (5) inflammatory invasion; (6) endothelial cell proliferation; and (7) Rho kinase activity.

B. Results

Treatment with BA-1049 (R) or treatment with a combination of Fasudil (Calbiochem)+BA-1049 (R) reduces the total number of lesions in 6 mo and 9 mo mice, in comparison with baseline (3 mo) results, and also reduces the total number of lesions, reduces the average lesion size and area, reduces the prevalence and proportion of stage 2 lesions, reduces the number of iron deposits near a given lesion, reduces the level of inflammatory invasion in a given cavern, reduces the endothelial cell proliferative index, and reduces Rho kinase activity in lesion endothelial cells, in comparison with control mice.

Pharmaceutical formulations with BA-1049 (R) and BA-1049 (R)+Fasudil are efficacious for treatment of individuals with an identified CCM.

Example 17

Prophylactic Reduction of Aneurysm Burden In Vivo

In these experiments, the efficacy of daily and weekly doses of BA-1049 (R) (NuChem Therapeutics) or Fasudil (Calbiochem) combinations as a prophylactic treatment to reduce overall intracranial aneurysm burden are tested.

A. Procedures

1. Intracranial Aneurysm Induction

At 2 mos of age, 96 female Sprague Dawley rats (Charles River Laboratories) weighing 130 g to 185 g undergo artery ligation and begin induced renal hypertension as follows, to facilitate the induction of intracranial aneurysms:

Before surgery, rats are anesthetized by intraperitoneal injection of pentobarbital (40 mg/kg). Rats undergo surgical ligation of the right common carotid artery, as well as surgical ligation of the bilateral posterior branches of the renal artery. A bilateral oophorectomy is performed following surgical ligation. Surgical ligation procedures are complemented by the addition of 1% NaCl to the drinking water from the day of surgery, as a means of inducing renal hypertension. Blood pressure is monitored weekly using a tail cuff Following the 2-mo surgical procedures, 24 rats are randomly assigned to each of the 3 test groups: (1) BA-1049 (R); (2) Fasudil; and (3) Control (see Table 16).

TABLE 16

| Aneurysm | Number of Rats | | |
|---|---|---|---|
| Prophylactic | Daily Dose | Weekly Dose | Total |
| BA-1049 (R) | 12 | 12 | 24 |
| Fasudil | 12 | 12 | 24 |
| Control | 12 | 12 | 24 |
| | Total | | 72 |

Half of the rats in each test group (12 animals/group) receive daily doses of the test article/control dissolved in 4 mL drinking water (1% NaCl) for a 2 mo period from the time of randomization. The control group receives a buffer vehicle. The other half of the rats in each test group (12 animals/group) receive weekly doses of the test article/control dissolved in 4 mL drinking water (1% NaCl) for a 2 mo period from the time of randomization. The control group receives a buffer vehicle. All rats are weighed immediately prior to dosing, to ensure an accurate calculation of the appropriate dose necessary to achieve the desired final concentration. At the end of the 24 hr period following a given dose, drinking water containers are monitored to ensure consumption of the full 4 mL (and so full test article dose).

After 2 mos of daily/weekly test article dosing, all rats undergo in vivo high-field MRI with a 14.1 T (600 MHz) imaging spectrometer. During this imaging, 3D-gradient recalled (GRE) images are acquired with a slice thickness of 250 μM, in-plane pixel size of 113 μM, repetition time (TR) of 100 ms, and echo time (TE) of 10 ms. All image sets are labeled with identification numbers to permit blinded analysis. After in vivo imaging, each rat is euthanized by $CO_2$ asphyxiation.

2. Preparation of Vascular Corrosion Casts

Following euthanasia, casts of the cerebral vasculature are prepared for ⅔ of the animals in each test group. For cast preparation, rats undergo laparotomy and thoracotomy. The tip of a plastic cannula (18-gauge, 1.25 inch) is inserted into the left ventricle and secured to the ascending aorta using a superimposed ligature. The right atrium is cut for drainage and rats are perfused with 100 mL heparinized (20 U/mL) phosphate-buffered saline at a rate of 10 mL/min. 10 mL of Batson No. 10 plastic (Polysciences, Inc., Warrington, Pa.) is manually injected into the vasculature and allowed to polymerize for 24 hr at room temperature (RT). The brain is removed and digested in potassium hydroxide. After 24 hr to 72 hr of digestion with intermittent water rinses, only a plastic cast of the cerebral vasculature remains. Vascular casts are labeled with an identification number to permit blinded analysis. The brains of the remaining third of the animals in each test group are isolated, fixed with formalin, and labeled with an identification number to permit blinded analysis.

3. Aneurysm Identification and Analysis

The prevalence and characteristics of saccular aneurysms in collected brains are analyzed by individuals blinded to the original dosing regimen and treatment group. Quantitative results for each analysis endpoint are calculated by two independent, blinded individuals and subsequently averaged. These endpoints are total number of aneurysms, aneurysm size, iron deposit formation, inflammatory invasion, and Rho kinase activity. The following sections discuss data collection and analysis for each endpoint used in aneurysm assessment.

The total number of saccular aneurysms is determined as follows: Saccular aneurysms are identified and counted using MRI imaging slices. In addition, as a complement to the MRI analysis, vascular corrosion casts are mounted onto the stage of a scanning electron microscope (SEM) using colloidal silver paste, sputter-coated with osmium. The total number of saccular aneurysms in the casted vasculature is quantified.

Aneurysm size is determined as follows: The maximal cross-sectional diameter of each saccular aneurysm (aneurysm size) is quantified based on an analysis of MRI slices. The maximal cross-sectional area of each aneurysm (area/ aneurysm), as well as the sum of the maximal cross-sectional areas of all aneurysms in a given animal (aneurysm area/brain) are also quantified. To complement the MM-based aneurysm analyses, sequential image slices of vascular corrosion casts are obtained using an SEM and the maximal cross-sectional diameter of each saccular aneurysm (aneurysm size), the maximal cross-sectional area of each saccular aneurysm (area/aneurysm), and the sum of the maximal cross-sectional areas of all saccular aneurysms in a given animal (aneurysm area/brain) are quantified.

MRI and vascular corrosion cast analyses are complemented by a histological analysis of coronal slices to identify iron deposit formation, inflammatory invasion, and Rho kinase activity in identified saccular aneurysms. For this analysis, isolated brains are cut into 14 1 mm thick coronal slices, from the olfactory bulbs at the frontal rostrum to the most caudal portion of the cerebellar hindbrain. Each slice is embedded in paraffin, sliced into 5 µM thick sections with a microtome, mounted onto charged microscope slides for hematoxylin and eosin staining, and then examined by independent assessors.

Perls' Prussian stain (Leica BioSystems) is used to assess iron deposits in the area surrounding each saccular aneurysm, as a marker of blood leakage from the aneurysm. Individual brain slices are treated with 30% hydrochloric acid and 10% potassium ferocyanide and counterstained with nuclear fast red. The number of Prussian blue iron deposits per aneurysm and proportion of aneurysms per brain with iron deposits is quantified.

As an additional marker of saccular aneurysm formation/severity, slices adjacent to those used in iron deposit analyses are stained by immunochemistry using primary antibodies for macrophages (mouse monoclonal anti-CD11b, (eBioscience, San Diego, Calif.) (14-0112-81), B cells (mouse monoclonal anti-B220) (BD Biosciences, San Jose, Calif.) (550286), plasma cells (mouse monoclonal anti-CD138 (BD Biosciences, San Jose, Calif.) (553712), and a biotinylated secondary antibody (Vector Laboratories, Burglingame Calif.) (BA 4000). The number of each type of inflammatory cell per saccular aneurysm is evaluated for each aneurysm and for the brain as a whole.

To assess relative levels of Rho kinase activity in the endothelial and smooth muscle cells of the saccular aneurysm wall, immunochemical slices are also stained for phosphorylated myosin light chain (pMLC, rabbit polyclonal anti-pMLC) and phosphorylated myosin basic subunit (pMBS, rabbit polyclonal anti-pMBS) (Cell Signaling Technology, Danvers, Mass.) (2634, 3671). Immunostaining of the vessel lining of each aneurysm is characterized as absent, weak, or strong and the proportion of 'absent' aneurysms and proportion of 'strong' aneurysms is calculated for each brain.

B. Results

Treatment with BA-1049 (R) or Fasudil reduces the total number of saccular aneurysms, reduces average aneurysm size and area, reduces the number of iron deposits near a given aneurysm, reduces the level of inflammatory invasion in a given aneurysm, and reduces Rho kinase activity in the endothelial and smooth muscle cells of the aneurysm wall, in comparison with control rats.

These results demonstrate the therapeutic efficacy of certain Rho kinase inhibitors alone or in combination with Fasudil in treating individuals with an identified aneurysm who are thus at a risk for future lesion development, as well as individuals with a known family history of intracranial aneurysm formation.

Example 18

Reduction of Prevalence/Size of Existing Aneurysms

The following experiments are designed to demonstrate the efficacy of BA-1049 (R) and of Fasudil as a treatment to reduce the size of existing saccular aneurysms or eliminate these aneurysms from the cerebral vasculature.

A. Procedures

1. Intracranial Aneurysm Induction

At 2 mos of age, female Sprague Dawley rats (Charles River Laboratories) weighing 130 g to 185 g undergo artery ligation and begin induced renal hypertension (as described in Example 18), to facilitate the induction of intracranial aneurysms.

Following the surgical procedures, 36 rats are randomly assigned to each of the 3 test groups: (1) BA-1049 (R) (2) Fasudil (Calbiochem); and (3) Control (see Table 17).

TABLE 17

| Aneurysm Treatment | Cohort 1[b] | Cohort 2 | Cohort 1 | Cohort 2 | |
|---|---|---|---|---|---|
| BA-1049 (R) | 12 | 6 | 12 | 6 | 36 |
| Fasudil | 12 | 6 | 12 | 6 | 36 |
| Control | 12 | 6 | 12 | 6 | 36 |
| | | Total | | | 108 |

[b]Cohort 1 is euthanized for analysis at 6 mos of age;
Cohort 2 is imaged and then euthanized at 8 mos of age.

After 2 mos of daily NaCl supplementation, the 4-mo old rats undergo baseline in vivo high-field MRI with a 14.1 T (600 MHz) imaging spectrometer. During this imaging, 3D-gradient recalled (GRE) images are acquired with a slice thickness of 250 µM, in-plane pixel size of 113 µM, repetition time (TR) of 100 ms, and echo time (TE) of 10 ms. All image sets are labeled with identification numbers to permit blinded analysis.

Half of the rats in each test group (18 animals/group) receive daily doses of the test composition/control dissolved in 4 mL drinking water (1% NaCl) for a 2 mo period from the time of baseline imaging (until 6 mos of age). The control group receives a buffer vehicle. The other half of the rats in each test group (18 animals/group) receive weekly doses of the test composition/control dissolved in 4 mL drinking water (1% NaCl) for a 2 mo period from the time of baseline imaging (until 6 mos of age). The control group receives a buffer vehicle. All rats are weighed immediately prior to dosing, to ensure an accurate calculation of the appropriate dose necessary to achieve the desired final concentration. At the end of the 24 hr period following a given dose, drinking water containers are monitored to ensure consumption of the full 4 mL (and so full test article dose).

After 2 mos of daily/weekly test article dosing, the 6 mo old rats undergo in vivo high-field MRI using the same procedures described for baseline imaging described above.

After the 6 mo MRI, animals in each dose regimen in each treatment group are divided into 2 cohorts. Cohort 1 is made up to two thirds of the animals receiving daily doses in each treatment group (12/18 animals)+two thirds of the animals receiving weekly doses in each treatment group (12/18 animals). Cohort 1 is used for vascular corrosion cast analyses+histological analyses of vehicle control vs treated aneurysms at 6 mos. Cohort 2 is made up of the remaining third of the animals receiving daily doses in each treatment group (6 animals)+the remaining third of the animals receiving weekly doses in each treatment group (6 animals). Cohort 2 is used to assess whether a treatment effect visible at 6 mos of age is still apparent at 8 mos of age.

After division into cohorts, Cohort 1 is euthanized by $CO_2$ asphyxiation. Vascular corrosion casts are prepared as described above for two thirds of the rats in each treatment group as described above in Example 18. The brains of the remaining third of the rats in each treatment group are removed, fixed in 10% formalin, and sectioned for histological analyses.

At 8 mos of age, Cohort 2 undergoes in vivo high-field MRI using the procedures described for baseline imaging.

After the 8 mos MRI, Cohort 2 is euthanized by $CO_2$ asphyxiation. Vascular corrosion casts are prepared for two thirds of the rats in each treatment group. The brains of the remaining third of the rats in each treatment group are removed, fixed in 10% formalin, and sectioned for histological analyses.

2. Primary Aneurysm Analysis

MRI slices are used to determine the change in aneurysm number and aneurysm size (area, diameter) from baseline to 6 mos of age in each mouse. For this analysis, the total number of saccular aneurysms, maximal cross-sectional diameter of each aneurysm, maximal cross-sectional area of each aneurysm (area/aneurysm), and sum of the maximal cross-sectional areas of all saccular aneurysms in a given animal (aneurysm area/brain) are quantified at baseline and at 6 mos. The changes from baseline to 6 mos in each category are calculated.

To analyze whether decreases in aneurysm diameter/area/number are maintained after completion of the dosing regimen, the 8 mo images from Cohort 2 are analyzed to permit a similar quantification of total saccular aneurysm number, aneurysm diameter, area/aneurysm, and aneurysm area/brain. Change from baseline to 8 mos in each category is quantified and compared with the change from baseline to 6 mos. Change from 6 mos to 8 mos in each category is also quantified. As described above in Example 18, quantitative results for each analysis endpoint are calculated by 2 independent, blinded individuals and subsequently averaged.

MRI-based primary analyses are complemented by histological/SEM analyses of coronal sections and vascular corrosion casts collected at 6 mos post injury in treated vs vehicle control rats from Cohort 1. To analyze whether changes last beyond cessation of treatment, Cohort 2 mouse brains collected at 9 mos post-injury are similarly analyzed.

SEM analyses of vascular corrosion casts are used to assess the same endpoints described in Example 18 for control vs treated rats at each timepoint: (1) total number of saccular aneurysms per brain; (2) saccular aneurysm size: maximal cross-sectional diameter/aneurysm, maximal cross-sectional area/aneurysm, and the total of the maximal cross-sectional areas of each aneurysm in a given brain.

Coronal sections are analyzed to assess the same endpoints described above in Example 18 for control vs treated rats at each timepoint: (1) iron deposits near aneurysm, (2) inflammatory invasion, and (3) Rho kinase activity in endothelial and smooth muscle cells of aneurysm wall.

B. Results

Treatment with BA-1049 (R) or Fasudil reduces the total number of saccular aneurysms in 6 mo and 8 mo rats, in comparison with baseline (4 mo) results. Treatment with BA-1049 (R) or Fasudil also reduces the total number of saccular aneurysms, reduces the average aneurysm size and area, reduces the number of iron deposits near a given aneurysm, reduces the level of inflammatory invasion in a given aneurysm, and reduces Rho kinase activity in the endothelial/smooth muscle cells of the aneurysm wall, in comparison with control rats.

These results demonstrate the therapeutic efficacy of inhibitors in the treatment of patients with an identified existing saccular aneurysm.

Example 19

Permeability of BA-1049 and Fasudil Through Caco-2 Cell Monolayers

An in vitro study was conducted to examine the ability of BA-1049 (racemic mixture) and Fasudil to cross Caco-2 cell monolayers. The permeabilities of [$^3$H]mannitol and [$^3$H] propranolol were determined in parallel as controls. In vitro examinations of Caco-2 cell monolayer transport offer guidance on whether a compound may be absorbed gastrointestinally in humans, an important factor in the consideration of whether a compound could potentially be developed as an orally active drug.

A. Procedures

1. Caco-2 Permeability Assay

Stock cultures of Caco-2 (ATCC Number: CRL-2002, clone of HTB-37) cells were maintained in MEM Earles medium (Invitrogen Corp., Carlsbad, Calif.) containing 10% fetal bovine serum (FBS) (Invitrogen Corp.), 0.1 mM non-essential amino acids (Invitrogen Corp.) and 1 mM sodium pyruvate (Invitrogen Corp.) at 37° C. in a humidified, 5% $CO_2$ atmosphere. Stock cultures were sub-cultured every 7 d when cells had reached 80%-90% confluency. Studies were conducted with Caco-2 cells, used at passage 34. Cells were plated on Transwell™ inserts (1 μm PET) (Becton-Dickinson Labware, Franklin Lakes, N.J.) at a density of 1×10$^4$ cells/well in 24-well culture plates. Cells were incubated at 37° C. under 5% $CO_2$ atmosphere, and media (MEM Earles medium containing 10% FBS, 0.1 mM non-essential amino acids and 1 mM sodium pyruvate) was changed 3 times per wk. Cells were used for permeability studies 21 d after seeding.

On the day of the assay, cell monolayers were washed 3 times. Each wash consisted of aspirating liquid from the apical (A) and basolateral (B) sides, and adding 0.5 and 1 mL, respectively, of fresh Dulbecco's phosphate-buffered saline with $Mg^{2+}$ and $Ca^{2+}$, pH 7.4 (PBS) (Invitrogen Corp.). After the final wash, a volt-ohm-meter (World Precision Instruments, Inc., Sarasota, Fla.) was used to determine the trans-epithelial electrical resistance (TEER), a measure of the integrity of the monolayer. Only cells with TEER values greater than 200 ohms/cm$^2$ were used.

A 35 μM working solution of each test compound was freshly prepared on the day of the experiment in Dulbecco's phosphate-buffered saline with $Mg^{2+}$ and $Ca^{2+}$, pH 7.4 (PBS). The concentrations of all solutions prepared for the drug candidates were corrected for the potency of the compounds (80.0% and 78.8% for Fasudil (Calbiochem) and BA-1049 (racemic mixture) (Synthetica Fine Chemicals), respectively). The D-[1-$^3$H(N)]Mannitol (17.0 Ci/mmol) PerkinElmer Life and Analytical Sciences, Boston, Mass.) and L-(−)-[4-$^3$H]propranolol (24.4 Ci/mmol) (PerkinElmer Life and Analytical Sciences) controls were prepared at a concentration of 1 μCi/mL, in PBS. The [$^3$H]propranolol solution was supplemented with unlabeled propranolol ((S)-(−)-propranol HCl) (Sigma-Aldrich Co., St. Louis, Mo.) for a final propranolol concentration of 100 μM.

For each test compound and standard, apical to basolateral (A to B) and basolateral to apical (B to A) transport was measured. The final volume on the basolateral side was 1 mL; the final volume on the apical side was 0.3 mL. The test compound working solution or radiolabeled standard solution was added to the 'donor' side. Blank buffer was added to the 'acceptor' side. Assays were carried out in duplicate on 24-well plates (Becton-Dickson Labware). Plates were incubated at 37° C. on a rotary shaker set at 150 rpm.

The permeability of each compound and control was measured by sampling 200 µL of medium from the acceptor compartment at time 0 and following 60 min incubation. A 100 µL sample was also taken from the donor compartment at the beginning of the study (immediately following addition to the donor compartment) and a 200 µL sample was also taken at the end of the incubation (60 min), for determination of mass balance.

All samples were placed in labeled 1.5 mL polypropylene tubes and stored frozen at −70° C. until bioanalysis. Prior to bioanalysis of the test compounds, 40 µL of the internal standard (IS) solution in mobile phase (20 ng/mL) was added to 10 µL of each sample. Samples were then centrifuged for 2 minutes at 10,000×g prior to injection of 10 µL of the supernatant into the LC-MS/MS instrument (Agilent 1100 Liquid Chromatograph with vacuum degasser (Model No. G1322A) (Agilent, Lexington, Mass.). A 100 µL aliquot of the samples containing the radiolabeled standards was added to 6.5 mL scintillation vials (Globe Scientific, Inc., New Jersey). A 3 mL aliquot of liquid scintillant (Ultima Gold, PerkinElmer Life and Analytical Sciences, Boston, Mass.) was added to the vials and disintegrations per minute (dpm) determined in a liquid scintillation counter (Tri-Carb 2000CA/LL, Canberra Packard, Canada).

2. Bioanalysis

A liquid chromatography tandem-mass spectrometry (LC-MS/MS) method was developed for the analysis of each test compound in PBS and pooled human plasma. LC-MS/MS was conducted using a PE Sciex API 4000 LC-MS/MS system equipped with an Agilent 1100 with a binary pump, solvent degasser and well plate autosampler, as well as a divert valve (VICI) (Valco Instrument Co., Inc., Baton Rouge, La.) installed between the column and mass spectrometer inlet. Sample cleanup of the plasma was performed by solid phase extraction. BA-1049 (racemic mixture) was used as an internal standard for Fasudil and vice versa.

A sample batch consisted of the following: calibration standards in ascending order (a blank sample (without internal standard), a zero sample (with internal standard), and six non-zero samples) and the assay samples. For the analysis of the PBS samples, samples were interspersed with one low, medium and high quality control sample. A batch was considered acceptable if both calibration curve acceptance criteria and quality control acceptance criteria were met. Acceptance criteria for the calibration curve standards were: not more than 15% deviation from the nominal value for accuracy, except for the limit of quantitation (LOQ) where 20% is acceptable, and a correlation coefficient (r) of≥0.99. Acceptance criteria for quality control samples were: within 20% accuracy for the LOQ and low concentration and 15% for the medium and high concentration quality controls. At least 2 out of 3 quality control samples must meet these criteria. Dilution quality controls are acceptable if they are within 20% accuracy of the target concentration.

3. Quantification of Permeability and Percent Recovery

The permeability coefficient ($P_{app}$) of each compound and radiolabeled standard was determined using the following equation:

$$P_{app} = \frac{dQ}{dT} \times 1/C_i \times 1/A$$

where dQ/dT represents the permeability rate, $C_i$ denotes the initial concentration in the donor compartment, and A represents the surface area of the filter. $C_i$ was determined from the mean concentration of duplicate samples taken immediately following the addition to the donor compartment. Permeability rates were calculated by plotting the cumulative amount of compound measured in the acceptor compartment over time and determining the slope of the line by linear regression analysis.

The % recovery (mass balance) of each compound and radiolabeled standard was determined using the following equation:

$$\% \text{ Recovery} = \frac{C_D V_D + C_A V_A}{C_i V_D} \times 100\%$$

where $C_D$ and $C_A$ represent the concentration of the compound or radiolabeled standard in the donor and acceptor compartments at the last sampling time-point (60 min), respectively, and $V_D$ and $V_A$ denote the volumes of the donor and acceptor compartments, respectively.

C. Results

Permeability coefficients ($P_{app}$) for Fasudil and BA-1049 (racemic mixture) transport across Caco-2 cell monolayers in the apical (A) to basolateral (B) and basolateral to apical direction are displayed in Table 18. Permeability coefficients for [$^3$H]mannitol and [$^3$H]propranolol are presented as controls: Mannitol, for which % absorption in humans is 15%, is known to permeate the Caco-2 cell layer through the paracellular route (i.e. diffusion through pores in the tight junctions between cells), as reflected by the low A to B and B to A $P_{app}$ values; Propranolol, known to permeate Caco-2 cells by passive transcellular diffusion, is by contrast well absorbed in humans (90%) and exhibits high $P_{app}$ values. The measured permeability coefficients of the control compounds were within the expected range from in-house data (26.2±8.10, A to B and 13.6±3.62, B to A for [$^3$H]mannitol and 323±54.0, A to B and 310±52.7, B to A for [$^3$H]propranolol). The measured $P_{app}$ values for BA-1049 indicate that it has intermediate to high Caco-2 cell permeability, whereas the $P_{app}$ values for Fasudil suggest that it has high Caco-2 cell permeability. The B to A/A to B $P_{app}$ ratios of the two compounds suggest that they are passively transported.

TABLE 18

| Compound | Initial Concentration (µM) | $P_{app}$ A to B (nm/s) | $P_{app}$ B to A (nm/s) | B-A/A-B $P_{app}$ Ratio |
|---|---|---|---|---|
| [$^3$H]-Mannitol | 0.0000241 | 10.1 ± 1.46 | 8.21 ± 3.62 | 0.81 |
| [$^3$H]-Propranolol | 100 | 360 ± 16.5 | 278 ± 36.8 | 0.77 |
| Fasudil | 41.4 | 189 | 185 | 0.98 |
| BA-1049 (Racemate) | 25.0 | 107 | 141 | 1.31 |

The fact that BA-1049 (racemic mixture) and Fasudil have intermediate to high permeability and are passively transported indicates that the drugs are well-absorbed in the human intestine. This supports the potential development of these compounds as orally active drugs.

Example 20

Binding of BA-1049 and Fasudil to Human Plasma Proteins

An in vitro study was conducted to quantify the percentage of BA-1049 (racemic mixture) and Fasudil bound to human plasma protein samples after 24 hr of dialysis. [³H]-propranolol and [³H]-warfarin were run in parallel as controls. In vitro examinations of plasma protein binding offer guidance on the levels of compound free for distribution/metabolism, an important factor in the consideration of whether a compound could potentially be developed as an orally active drug.

A. Procedures

1. Equilibrium Dialysis

To 0.990 mL of thawed plasma (heparinized (lithium heparin) pooled mixed-gender human plasma) (Biochemed Pharmacologicals, Inc., Winchester, Va.) thawed at 37° C., a 10 μL aliquot of the stock solutions was added for test compound (Fasudil (Calbiochem) and BA-1049 (racemic mixture) (Synthetica Fine Chemicals) concentrations of 35 μM. An appropriate volume of buffer (Dulbecco's phosphate buffered saline, pH 7.4) (Invitrogen Corp.) was also spiked with each test compound at a concentration of 35 μM. Duplicate aliquots (130 μL) of each spiked plasma and buffer solution were collected prior to dialysis into labeled 1.5 mL polypropylene tubes and stored frozen at −70° C. The standards, L-(−)-[4-³H]propranolol (24.4 Ci/mmol) (Perkin Elmer, Boston, Mass.) and [phenyl-4-³H]-(R,S)-Warfarin (15 Ci/mmol, Moravek Biochemicals Inc., Brea, Calif.), were prepared in plasma at a concentration of 1 μCi/mL.

Equilibrium dialysis was performed in a 96-well Teflon dialysis unit (HTDialysis LLC, Gales Ferry, Conn.). Each well of the unit consisted of two chambers separated by a vertically aligned dialysis membrane (regenerated cellulose) with a molecular weight cut-off of 12-14 KDa (HTDialysis LLC). The equilibrium dialysis membranes were first pre-soaked in deionized water for 30 min, then soaked in 20% ethanol for 20 min, followed by rinsing twice with deionized water.

The equilibrium dialysis apparatus was assembled according to the manufacturer's directions. One chamber of each well was immediately filled with 150 μL of blank buffer (to prevent membrane dehydration). Aliquots (150 μL) of spiked plasma or spiked buffer were then added to the opposing chamber in each well. The top of the plate was sealed with an adhesive sealing film (HTDialysis LLC) to prevent evaporation and maintain constant pH during incubation.

The dialysis apparatus was incubated at 37° C. in an orbital shaker/incubator (Lab-Line Enviro Shaker) set at 150 rpm. An aliquot (100 μL) from each plasma and buffer compartment was collected following 24 hr incubation. Samples containing the test compounds were stored frozen at −70° C. Samples (100 μL) containing the radiolabeled standards were added to 6.5 mL scintillation vials (Globe Scientific Inc., N.J.), to which 3 mL of liquid scintillant (Ultima Gold, PerkinElmer Life and Analytical Sciences, Boston, Mass.) was added and mixed by vortex. The disintegrations per minute (dpm) in each vial were measured with a liquid scintillation counter (Tri-Carb 2000CA/LL) (Canberra Packard).

All dialysis experiments with the test compounds and standards were assessed using duplicate samples.

2. Bioanalysis

Plasma concentrations in the aliquots collected after 24 hr of dialysis were analyzed by LC-MS/MS using the methods described in Example 20.

3. Quantification of Unbound Fraction and Percent Recovery

The fraction of each test compound and standard unbound ($f_u$) to human serum proteins was calculated according to the following equation:

$$f_u = \frac{C_{buffer}}{C_{plasma}}$$

where $C_{buffer}$ and $C_{plasma}$ represent the concentration of the compound measured in the buffer and plasma chambers, respectively, following dialysis. The fraction bound ($f_b$) to the plasma proteins was determined as: $1-f_u$. The recovery (mass balance) of the compounds and standards from the dialysis apparatus was calculated as:

$$\text{Recovery (\%)} = \frac{C_{plasma}V_{plasma} + C_{buffer}V_{buffer}}{C_{plasma}(t=0)V_{plasma}} \times 100\%$$

where $C_{plasma}$ (t=0) represents the concentration of the compound measured in plasma prior to dialysis, and $V_{plasma}$ and $V_{buffer}$ represent the volumes of plasma and buffer, respectively, that were added to the opposing sides of the dialysis chambers.

The data are expressed as the mean for 2 replicate samples.

B. Results

Plasma protein binding results for Fasudil and BA-1049 (racemic mixture) (Synthetica Fine Chemicals) are presented in Table 19. For reference, the plasma binding properties of [³H]mannitol and [³H]propranolol controls are presented as well; propranolol is known to bind to $\alpha_1$-acid glycoprotein, whereas warfarin binds to Site 1 on albumin. The percentage of Fasudil bound to human plasma proteins was determined to be 19.2% and the percentage of BA-1049 bound to human plasma proteins was determined to be 7.26%. Recovery of Fasudil and BA-1049 following 24 hr of dialysis was essentially complete. The results for both propranolol and Warfarin are consistent with those quoted in the literature as well as with in-house data previously generated for human plasma (87.9±0.996 and 99.2±0.222% bound (n=3) for propranolol and warfarin, respectively).

TABLE 19

| Compound ID | Plasma Concentration[a] (ng/mL) | Unbound (%) | Bound (%) | Recovery (%) |
| --- | --- | --- | --- | --- |
| (S)-Propranolol | 72.8[b] | 8.67 | 91.3 | 73.9 |
| (R, S)-Warfarin | 160[b] | 0.895 | 99.1 | 72.9 |
| Fasudil | 5180 | 81.8 | 19.2 | 114 |
| BA-1049 (Racemate) | 5575 | 92.7 | 7.26 | 98.1 |

[a]Plasma concentrations measured following 24 h of dialysis.
[b]Concentration reported as pM.

The proportion of BA-1049 (racemic mixture) and Fasudil unbound to human plasma protein samples indicates availability for distribution/metabolism. This supports the utility of BA-1049 (racemic mixture) and Fasudil as orally active compounds.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating a cerebral cavernous malformation (CCM) in a mammal, comprising:
administering to the mammal a therapeutically effective amount of a pharmaceutical formulation comprising BA-1049; and
detecting a reduction in the number or size of CCM lesions and/or maturation of simple CCM lesions into complex, clinically significant lesions relative to the number, size, and/or maturity of CCM lesions before administration.

2. The method of claim 1, wherein the BA-1049 is a racemic mixture.

3. The method of claim 1, wherein the BA-1049 is the (R) enantiomer.

4. The method of claim 1, wherein the pharmaceutical formulation is administered orally.

5. The method of claim 4, wherein the pharmaceutical formulation is in the form of a tablet or a capsule.

6. The method of claim 1, wherein the method further comprises administering to the mammal a therapeutically effective amount of at least a second Rho kinase inhibitor other than BA-1049 (racemic mixture) or BA-1049 (R).

7. The method of claim 6, wherein the at least a second Rho kinase inhibitor is BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853, and/or Y27632.

8. The method of claim 1, wherein the pharmaceutical formulation further comprises at least a second Rho kinase inhibitor other than BA-1049 (racemic mixture) or BA-1049 (R).

9. The method of claim 8, wherein the at least a second Rho kinase inhibitor is BA-1042, BA-1043, BA-1044, BA-1050, BA-1051, C3, KD025, Rhopressa, Roclatan, AR-13533, Fasudil, HA-1077, Radicut, Azandoile 1, BF66851, BF66852, BF66853 and/or Y27632.

10. The method of claim 4, wherein the pharmaceutical formulation is in the form of a tablet.

* * * * *